United States Patent [19]
Yu et al.

[11] Patent Number: 6,013,504
[45] Date of Patent: Jan. 11, 2000

[54] α-1,4-GLUCAN LYASE FROM A FUNGUS INFECTED ALGAE, ITS PURIFICATION, GENE CLONING AND EXPRESSION IN MICROORGANISMS

[75] Inventors: Shukun Yu, Malmo, Sweden; Kirsten Bojsen, Allerod, Denmark; Karsten Kragh, Viby, Denmark; Maja Bojko, Gentofte, Denmark; John Nielsen; Jan Marcussen, both of Copenhagen, Denmark

[73] Assignee: Danisco A/S, Copenhagen, Denmark

[21] Appl. No.: 08/633,768

[22] PCT Filed: Oct. 15, 1994

[86] PCT No.: PCT/EP94/03399

§ 371 Date: Jul. 2, 1996

§ 102(e) Date: Jul. 2, 1996

[87] PCT Pub. No.: WO95/10618

PCT Pub. Date: Apr. 20, 1996

[30] Foreign Application Priority Data

Oct. 15, 1993 [GB] United Kingdom ............... 9321301

[51] Int. Cl.$^7$ ..................................................... C12N 9/88
[52] U.S. Cl. .................. 435/232; 435/105; 435/252.3; 435/252.33; 435/257.2; 536/23.1; 536/23.2; 536/23.74; 424/94.5
[58] Field of Search .................. 435/232, 257.2, 435/252.3, 252.33, 105; 536/23.1, 23.2, 23.74; 424/94.5

[56] References Cited

FOREIGN PATENT DOCUMENTS

WO09122  4/1994  WIPO .

OTHER PUBLICATIONS

Ujhazi et al. Proc. of the fourth international symposium on cyclodextrin, Huber et al. (eds), pp. 497–501, 1988.
Baute et al. Bull. Soc. Pharm. Bordeaux. 128, 1–4, 9–18 English abstract, 1989.
Sanger, F., et al. "DNA sequencing with chain-terminating inhibitors" *Proc. Natl. Acad. Sci. USA* vol. 74, No. 12, pp. 5463–5467, Dec. 1977.
Baxten, F. P., et al. "Transformation of *Aspergillus niger* using the argb gene of *Aspergillus nidulans*" *Gene* vol. 37, pp. 207–214, 1985.
Collinge, D. B., et al. "Gene expression in Brassica campestris showing a hypersensitive . . . " *Plant Molecular Biology* vol. 8, pp. 405–414, 1987.
Frohman, M. A., et al. "Rapid production of full-length cDNAs from . . . " *Proc. Natl. Acad. Sci. USA* vol. 85, pp. 8998–9002, Dec. 1988.
Langdale, J.A., et al. "Cellular pattern of photosynthetic gene expression in developing maize . . . " *Genes and Development* vol. 2, pp. 106–115, 1988.
Pueschel, C. M., "An expanded survey of the ultrastructure of red algal pit plugs" *J. Phycol* vol. 25, pp. 625–636, 1989.
Punt, P. J., et al., "Intracellular and extracellular production of proteins in . . . " *Journal of Biotechnology* vol. 17, pp. 19–34, 1991.
Punt, P. J., et al., Transformation of Filamentous Fungi Based on Hygromycin . . . *Methods in Enzymology* vol. 216, pp. 447–457, 1992.
Archer, D. B., et al. "Proteolytic degradation of heterologous proteins expressed in *aspergillus niger*" *Biotechnology Letters* vol. 14, pp. 357–362.
Saunders, G. W., "Gel purification of red algal genomic DNA: An inexpensive and rapid method . . . " *J. Phycol.* vol. 29, pp. 251–254, 1993.
LeGendre, N., et al. "Purification of proteins . . . " *A practical guide to protein and peptide purification for microsequencing* 2nd Edit. pp. 74–101.
Pall, M. L., et al. "A series of six compact fungal transformations vectors containing polylinkers . . . " *Fungal Genet Newslett* vol. 40, pp. 59–62.
Yu, et al., BA Biochimica et Biohysica Acta, Elsevier Science, "a–1,4–Glucan lyase, a new class of starch/glycogen degrading enzyme," 1156:313–320, (1993).
Shukun Yu and Marianne Pedersen, Planta, "a–1,4, Glycan lyase, a new class of starch/glycogen–degrading enzyme," 191:137–143, (1993).
Plant Physiology, Biochemistry and Biophysics, Bio. Abstr. 57: AB–926, No. 52735, referencing Baute et al., Phytochemistry, 27:3401–3403 (1988).
Baute, et al., Phytochemistry, "Fungal Enzymic Activiity Degrading 1,4–a–D–Glucans to 1,5–D–Anhydrofructose," 27:3401–3403 (1988).

*Primary Examiner*—Robert A. Wax
*Assistant Examiner*—Nashaat T. Nashed
*Attorney, Agent, or Firm*—Knobbe, Martens, Olson & Bear, LLP

[57] ABSTRACT

A method of preparing α-1,4-glucan lyase enzymes is described. The method comprises isolating the enzymes from a fungally infected algae. The amino acid sequences of the enzymes have been determined. The nucleic acid sequences coding for the enzymes have also been determined.

7 Claims, 15 Drawing Sheets

SEQ ID No.1

MFSTLAFVAP SALGASTFVG AEVRSNVRIH SAFPAVHTAT RKTNRLNVSM TALSDKQTAT
AGSTDNPDGI DYKTYDYVGV WGFSPLSNTN WFAAGSSTPG GITDWTATMN VNFDRIDNPS
ITVQHPVQVQ VTSYNNNSYR VRFNPDGPIR DVTRGPILKQ QLDWIRTQEL SEGCDPGMTF
TSEGFLTFET KDLSVIIYGN FKTRVTRKSD GKVIMENDEV GTASSGNKCR GLMFVDRLYG
NAIASVNKNF RNDAVKQEGF YGAGEVNCKY QDTYILERTG IAMTNYNYDN LNYNQWDLRP
PHHDGALNPD YYIPMYYAAP WLIVNGCAGT SEQYSYGWFM DNVSQSYMNT GDTTWNSGQE
DLAYMGAQYG PFDQHFVYGA GGGMECVVTA FSLLQGKEFE NQVLNKRSVM PPKYVFGFFQ
GVFGTSSLLR AHMPAGENNI SVEEIVEGYO NNNFPFEGLA VDVDMODNLR VFTTKGEFWT
ANRVTGGDP NNRSVFEWAH DKGLVCQTNI TCFLRNDNEG QDYEVNQTLR ERQLYTKNDS
LTGTDFGMTD DGPSDAYIGH LDYGGGVECD ALFPDWGRPD VAEWWGNNYK KLFSIGLDFV
WQDMTVPAMM PHKIGDDINV KPDGNWPNAD DPSNGQYNWK TYHPQVLVTD MRYENHGREP
MVGTQRNIHAY TLCESTRKEG IVENADTLTK FRRSYIISRG GYIGNQHFGG MWVGDNSTTS
NYIQMMIANN INMNMSCLPL VGSDIGGFTS YDNENQRTPC TGDLMVRYVQ AGCLLPWFRN
HYDRWIESKD HGKDYQELYM YPNEMDTLRK FVEFRYRWQE VLYTAMYQNA AFGKPIIKAA
SMYNNDSNVR RAQNDHFLLG GHDGYRILCA PVVWENSTER ELYLPVLTQW YKFGPDFDTK
PLEGAMNGGD RIYNYPVPQS ESPIFVREGA ILPTRYTLNG ENKSLNTYTD EDPLVFEVFP
LGNNRADGMC YLDDGGVTTN AEDNGKFSVV KVAAEQDGGT ETITFTNDCY EYVFGGPFYV
RVRGAQSPSN IHVSSGAGSQ DMKVSSATSR AALFNDGENG DFWVDQETDS LWLKLPNVVL
PDAVITIT

FIG.7

```
GL1 -  MFSTLAFVAPSALGASTFVGAEV-RSNVRIHSAFPAVHTATRKTNRLNVS   -  49   SEQ ID No.1
GL2 -  MYPTLTFVAPSALGARTFTCVGIFRSHILIHSVVPAVRLAVRKSNRLNVS   -  50   SEQ ID No.2

GL1 -  MTALSDKQTATAGSTDNPDGIDYKTYDYVGVWGFSPLSNTNWFAAGSSTP   -  99
GL2 -  MSALFDKPTAVTGGKDNPDNINYTTYDYVPVWRFDPLSNTNWFAAGSSTP   - 100

GL1 -  GGITDWTATMNVNFDRIDNPSITVQHPVQVQVTSYNNNSYRVRFNPDGPI   - 149
GL2 -  GDIDDWTATMNVNFDRIDNPSFTLEKPVQVQVTSYKNNCFRVRFNPDGPI   - 150

GL1 -  RDVTRGPILKQQLDWIRTQELSEGCDPGMTFTSEGFLTFETKDLSVIIYG   - 199
GL2 -  RDVDRGPILQQQLNWIRKQEQSKGFDPKMGFTKEGFLKFETKDLNVIIYG   - 200

GL1 -  NFKTRVTRKSDGKVIMENDEVGTASSGNKCRGLMFVDRLYGNAIASVNKN   - 249
GL2 -  NFKTRVTRKRDGKGIMENNEVPAGSLGNKCRGLMFVDRLYGTAIASVNEN   - 250

GL1 -  FRNDAVKQEGFYGAGEVNCKYQDT------YILERTGIAMTNYNYDNLNY   - 293
GL2 -  YRNDPDRKEGFYGAGEVNCEFWDSEQNRNKYILERTGIAMTNYNYDNYNY   - 300

GL1 -  NQWDLRPPHHDGALNPDYYIPMYYAAPWLIVNGCAGTS-EQYSYGWFMDN   - 342
GL2 -  NQSDLIAP--GYPSDPNFYIPMYFAAPWVVKGCSGNSDEQYSYGWFMDN   - 348

GL1 -  VSQSYMNTGDTTWNSGQEDLAYMGAQYGPFDQHFVVGAGGMECVVTAFS    - 392
GL2 -  VSQTYMNTGGTSWNCGEENLAYMGAQCGPFDQHFVVGDGDGLEDVVQAFS  - 398

GL1 -  LLQGKEFENQVLNKRSVMPPKYVFGFFQGVFGTSSLLRAHMPAGENNISV  - 442
```

FIG. 8a

| | | |
|---|---|---|
| GL2 | LLQGKEFENQVLNKRAVMPPKYVFGYFQGVFGIASLLREQRPEGGNNISV | 448 |
| GL1 | EEIVEGYQNNNFPFEGLAVDVDMQDNLRVFTTKGEFWTANRVGTGGDPNN | 492 |
| GL2 | QEIVEGYQSNNFPLEGLAVDVDMQQDLRVFTTKIEFWTANKVGTGGDSNN | 498 |
| GL1 | RSVFEWAHDKGLVCQTNITCFLRNDNEGQDYEVNQTLRERQLYTKNDSLT | 542 |
| GL2 | KSVFEWAHDKGLVCQTNVTCFLRNDNGGADYEVNQTLREKGLYTKNDSLT | 548 |
| GL1 | GTDFGMTDDGPSDAYIGHLDYGGGVECDALFPDWGRPDVAEWWGNNYKKL | 592 |
| GL2 | NTNFGTTNDGPSDAYIGHLDYGGGGNCDALFPDWGRPGVAEWWGDNYSKL | 598 |
| GL1 | FSIGLDFVWQDMTVPAMMPHKIGDDINVKPDGNWPNADDPSNGQYNWKTY | 642 |
| GL2 | FKIGLDFVWQDMTVPAMMPHKVGDAVDTRSPYGWPNENDPSNGRYNWKSY | 648 |
| GL1 | HPQVLVTDMRYENHGREPMVTQRNIHAYTLCESTRKEGIVENADTLTKFR | 692 |
| GL2 | HPQVLVTDMRYENHGREPMFTQRNMHAYTLCESTRKEGIVANADTLTKFR | 698 |
| GL1 | RSYIISRGGYIGNQHFGGMWVGDNSTTSNYIQMMIANNINMNMSCLPLVG | 742 |
| GL2 | RSYIISRGGYIGNQHFGGMWVGDNSSSQRYLQMMIANIVNMNMSCLPLVG | 748 |
| GL1 | SDIGGFTSYDNENQRTPCTGDLMVRYVQAGCLLPWFRNHYDRWIESKDHG | 792 |
| GL2 | SDIGGFTSYDG--RNVCPGDLMVRFVQAGCLLPWFRNHYGRLVEGKQEG | 795 |
| GL1 | KDYQELYMYPNEMDTLRKFVEFRYRWQEVLYTAMYQNAAFGKPIIKAASM | 842 |
| GL2 | KYYQELYMYKDEMATLRKFIEFRYRWQEVLYTAMYQNAAFGKPIIKAASM | 845 |

FIG. 8b

```
GL1  -  YNNDSNVRRAQNDHFLLGGHDGYRILCAPVVWENSTERELYLPVLTQWYK  -  892
GL2  -  YDNDRNVRGAQDDHFLLGGHDGYRILCAPVVWENTTSRDLYLPVLTKWYK  -  895

GL1  -  FGPDFDTKPLEGAMNGGDRIYNYPVPQSESPIFVREGAILPTRYTLNGEN  -  942
GL2  -  FGPDYDTKRLDSALDGGQMIKNYSVPQSDSPIFVREGAILPTRYTLDGSN  -  945

GL1  -  KSLNTYTDEDPLVFEVFPLGNNRADGMCYLDDGGVTTNAEDNGKFSVVKV  -  992
GL2  -  KSMNTYTDKDPLVFEVFPLGNNRADGMCYLDDGGITTDAEDHGKFSVINV  -  995

GL1  -  AAEQDGGTETITFTNDCYEYVFGGPFYVRVRGAOSPSNIHVSSGAGSQDM  -  1042
GL2  -  EALRKGVTTTIKFAYDTYQYVFDGPFYVRIRNLTTASKINVSSGAGEEDM  -  1045

GL1  -  KVSSATSRAALFNDGENGDFWVDQETDSLWLKLPNVVLPDAVITIT  -  1088
GL2  -  TPTSANSRAALFSDGGVGEYWADNDTSSLWMKLPNLVLQDAVITIT  -  1091
```

FIG. 8c

α-1,4-GLUCAN LYASE FROM A FUNGUS INFECTED ALGAE, ITS PURIFICATION, GENE CLONING AND EXPRESSION IN MICROORGANISMS

The present invention relates to an enzyme, in particular α-1,4-glucan lyase ("GL"). The present invention also relates to a method of extracting the same. The present invention also relates to nucleotide sequence(s) encoding for the same.

FR-A-2617502 and Baute et al in Phytochemistry [1988] vol. 27 No. 11 pp3401–3403 report on the production of 1,5-D-anhydrofructose ("AF") in *Morchella vulgaris* by an apparent enzymatic reaction. The yield of production of AF is quite low. Despite a reference to a possible enymatic reaction, neither of these two documents presents any amino acid sequence data for any enzyme, let alone any nucleotide sequence information. These documents say that AF can be a precursor for the preparation of the antibiotic pyrone microthecin.

Yu et al in Biochimica et Biophysica Acta [1993] vol 1156 pp313–320 report on the preparation of GL from red seaweed and its use to degrade α-1,4glucan to produce AF. The yield of production of AF is quite low. Despite a reference to the enzyme GL this document does not present any amino acid sequence data for that enzyme let alone any nucleotide sequence information coding for the same. This document also suggests that the source of GL is just algal.

According to the present invention there is provided a method of preparing the enzyme α-1,4-glucan lyase comprising isolating the enzyme from a fungally infected algae.

Preferably the enzyme is isolated and/or further purified using a gel that is not degraded by the enzyme.

Preferably the gel is based on dextrin, preferably beta-cyclodextrin, or derivatives thereof, preferably a cyclodextrin, more preferably beta-cyclo-dextrin.

According to the present invention there is also provided a GL enzyme prepared by the method of the present invention.

Preferably the enzyme comprises the amino acid sequence SEQ. ID. No. 1. or SEQ. ID. No. 2, or any variant thereof.

The term "any variant thereof" means any substitution of, variation of, modification of, replacement of, deletion of or addition of at least one amino acid from or to the sequence providing the resultant enzyme has lyase activity.

According to the present invention there is also provided a nucleotide sequence coding for the enzyme α-1,4-glucan lyase, preferably wherein the sequence is not in its natural environment (i.e. does not form part of the natural genome of a cellular organism expressing the enzyme).

Preferably the nucleotide sequence is a DNA sequence.

Preferably the DNA sequence comprises a sequence that is the same as, or is complementary to, or has substantial homology with, or contains any suitable codon substitution(s) for any of those of, SEQ. ID. No. 3 or SEQ. ID. No. 4.

The expression "substantial homology" covers homology with respect to structure and/or nucleotide components and/or biological activity.

The expression "contains any suitable codon substitutions" covers any codon replacement or substitution with another codon coding for the same amino acid or any addition or removal thereof providing the resultant enzyme has lyase activity.

In other words, the present invention also covers a modified DNA sequence in which at least one nucleotide has been deleted, substituted or modified or in which at least one additional nucleotide has been inserted so as to encode a polypeptide having the activity of a glucan lyase, preferably an enzyme having an increased lyase activity.

According to the present invention there is also provided a method of preparing the enzyme α-1,4-glucan lyase comprising expressing the nucleotide sequence of the present invention.

According to the present invention there is also provided the use of beta-cyclodextrin to purify an enzyme, preferably GL.

According to the present invention there is also provided a nucleotide sequence wherein the DNA sequence comprises a sequence that is the same as, or is complementary to, or has substantial homology with, or contains any suitable codon substitutions for any of those of, SEQ. ID. No. 3 or SEQ. ID. No. 4, preferably wherein the sequence is in isolated form.

A key aspect of the present invention is the recognition that GL is derived from a fungally infected algae. This is the first time that the amino acid sequence of GL has been determined in addition to the determination of the nucleic acid sequences that code for GL. A key advantage of the present invention is therefore that GL can now be made in large quantities by for example recombinant DNA techniques and thus enable compounds such as the antibiotic microthecin to be made easily and in larger amounts.

The enzyme should preferably be secreted to ease its purification. To do so the DNA encoding the mature enzyme is fused to a signal sequence, a promoter and a terminator from the chosen host.

For expression in *Aspergillus niger* the gpdA (from the Glyceraldehyde-3-phosphate dehydrogenase gene of *Aspergillus nidulans*) promoter and signal sequence is fused to the 5' end of the DNA encoding the mature lyase—such as SEQ I.D. No. 3 or SEQ. I.D. No.4. The terminator sequence from the *A. niger* trpC gene is placed 3' to the gene (Punt, P. J. et al (1991): J. Biotech. 17, 19–34). This construction is inserted into a vector containing a replication origin and selection origin for *E. coli* and a selection marker for *A. niger*. Examples of selection markers for *A. niger* are the amdS gene, the argB gene, the pyrG gene, the hygB gene, the BmlR gene which all have been used for selection of transformants. This plasmid can be transformed into *A. niger* and the mature lyase can be recovered from the culture medium of the transformants.

The construction can be transformed into a protease deficient strain to reduce the proteolytic degradation of the lyase in the culture medium (Archer D. B. et al (1992): Biotechnol. Lett. 14, 357–362).

Other advantages will become apparent in the light of the following description.

The present invention therefore relates to the isolation of the enzyme α-1,4-glucan lyase from a fungus infected algae—preferably a fungus infected red algae such as the type that can be collected in China—such as *Gracilariopsis lemaneiformis*. An example of a fungally infected algae has been deposited in accordance with the Budapest Treaty (see below).

By using in situ hybridisation technique it was established that the enzyme GL was detected in the fungally infected red algae *Gracilariopsis lemaneiformis*. Further evidence that supports this observation was provided by the results of Southern hybridisation experiments. Thus GL enzyme activity can be obtained from fungally infected algae, rather than just from the algae as was originally thought.

Of particular interest is the finding that there are two natural DNA sequences, each of which codes for an enzyme having GL characteristics. These DNA nucleic acid sequences have been sequenced and they are presented as SEQ. I.D. No. 3 and SEQ. I.D. No. 4 (which are discussed and presented later).

An initial enzyme purification can be performed by the method as described by Yu et al (ibid). However, it is preferred that the initial enzyme purification includes the use of a solid support that does not decompose under the purification step. This gel support has the advantage that it is compatible with standard laboratory protein purification equipment. The details of this preferred purification process are given later on. The purification is terminated by known standard techniques for protein purification. The purity of the enzyme was established using complementary electroforetic techniques.

The purified lyase was characterized according to pI, temperature- and pH-optima. In this regard, it was found that the enzyme has the following characteristics: an optimum substrate specificity and a pH optimum at 3.5–7.5 when amylopectin is used; a temperature optimum at 50° C. and a pI of 3.9.

As mentioned above, the enzymes according to the present invention have been determined (partially by amino-acid sequencing techniques) and their amino acid sequences are provided later. Likewise the nucleotide sequences coding for the enzymes according to the present invention (i.e. GL) have been sequenced and the DNA sequences are provided later.

The following samples were deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on Jun. 20, 1994:

E. Coli containing plasmid pGL1 (NCIMB 40652)—[ref. DH5alpha-pGL1]; and

E. Coli containing plasmid pGL2 (NCIMB 40653)—[ref. DH5alpha-pGL2].

The following sample was accepted as a deposit in accordance with the Budapest Treaty at the recognised depositary The Culture Collection of Algae and Protozoa (CCAP) at Dunstaffnage Marine Laboratory PO Box 3, Oban, Argyll, Scotland, United Kingdom, PA34 4AD on Oct. 11, 1994:

Fungally infected *Gracilariopsis lemaneiformis* (CCAP 1373/1)—[ref. GLQ-1 (Qingdao)].

Thus highly preferred embodiments of the present invention include a GL enzyme obtainable from the expression of the GL coding sequences present in plasmids that are the subject of either deposit NCIMB 40652 or deposit NCIMB 40653; and a GL enzyme obtainable from the fungally infected algae that is the subject of deposit CCAP 1373/1.

The present invention will now be described only by way of example.

In the following Examples reference is made to the accompanying figures in which:

FIGS. 1a and 1b shows stained fungally infected algae;
FIG. 2 shows stained fungally infected algae;
FIGS. 3a–d shows sections of fungally infected algae;
FIG. 4 shows a section of fungally infected algae;
FIG. 5 shows a plasmid map of pGL1;
FIG. 6 shows a plasmid map of pGL2;
FIG. 7 shows the amino acid sequence represented as SEQ. I.D. No.3 showing positions of the peptide fragments that were sequenced;.
FIGS. 8a–c shows the alignment of SEQ. I.D. No. 1 with SEQ. I.D. No.2;
FIG. 9 is a microphotograph.

In more detail, FIGS. 1a and 1b shows Calcoflour White stainings revealing fungi in upper part and lower part of *Gracilariopsis lemaneiformis* (108× and 294×).

FIG. 2 shows PAS/Anilinblue Black staining of *Gracilariopsis lemaneiformis* with fungi. The fungi have a significant higher content of carbohydrates.

FIGS. 3a–d shows the antisense detections with clone 2 probe (a and b) appear to be restricted to the fungi illustrated by Calcoflour White staining of the succeeding section (c and d) (46× and 108×).

FIGS. 8a–c shows the alignment of SEQ. I.D. No. 1 (GL1) with SEQ. I.D. No.2 (GL2). The total number of residues for GL1 is 1088; and the total number of residues for GL2 is 1091. In making the comparison, a structure-genetic matrix was used (Open gap cost: 10; Unit gap cost: 2). In FIGS. 8a–c the character to show that two aligned residues are identical is ':'; and the character to show that two aligned residues are similar is '.'. Amino acids said to be 'similar' are: A,S,T; D,E; N,Q; R,K; I,L,M,V; F,Y,W. Overall there is an identity of 845 amino acids (i.e. 77.67%); a similarity of 60 amino acids (5.51%). The number of gaps inserted in GL1 are 3 and the number of gaps inserted in GL2 are 2.

Figure 9:
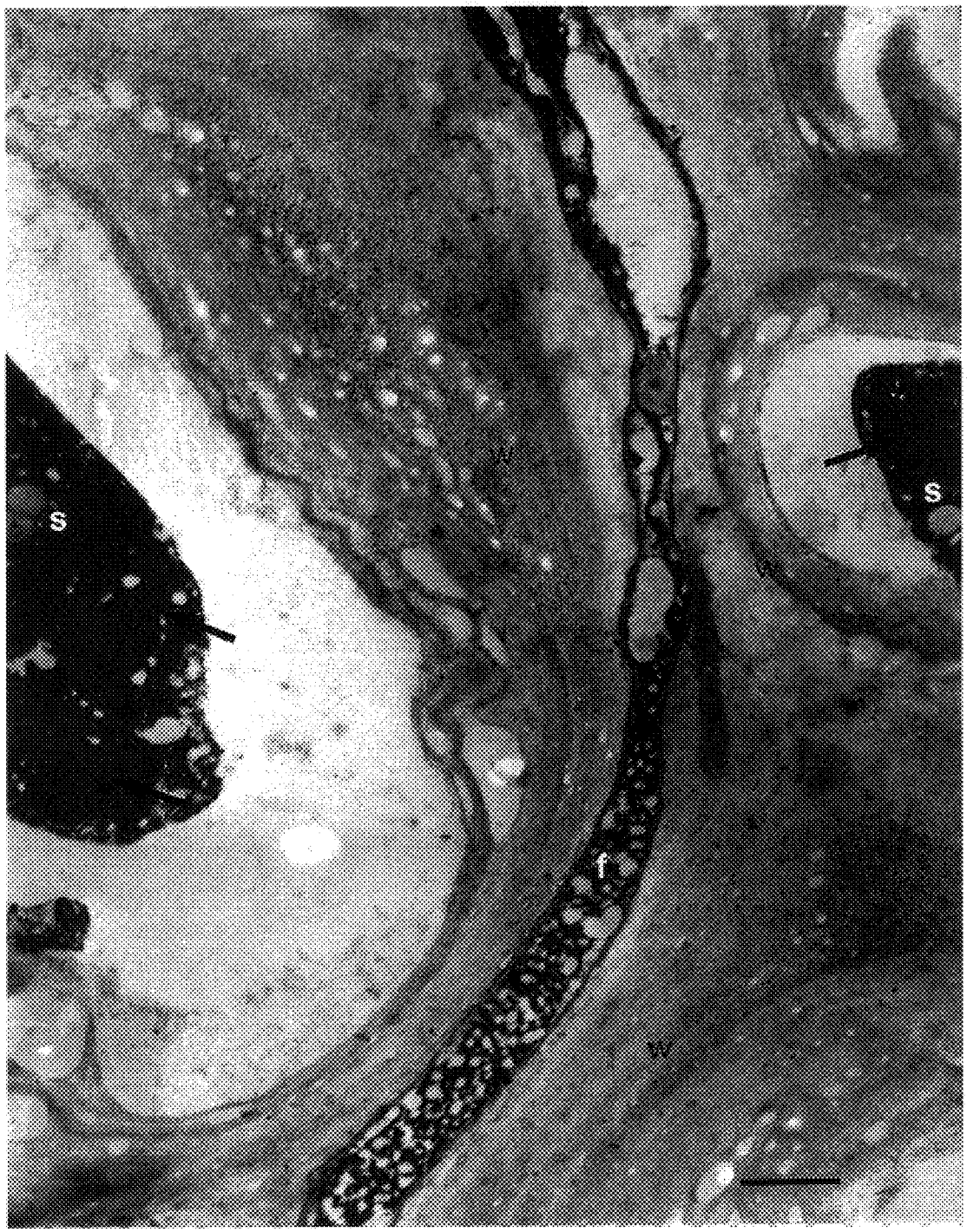

FIG. 9 is a microphotograph of a fungal hypha (f) growing between the algal walls (w). Note grains of floridean starch (s) and thylakoids (arrows) in the algal cell.

The following sequence information was used to generate primers for the PCR reactions mentioned below and to check the amino acid sequence generated by the respective nucleotide sequences.

```
Amino acid sequence assembled from peptides from fungus infected Gracilariopsis
                                  lemaneiformis Tyr Arg Trp Gln Glu Val Leu Tyr Thr Ala Met Tyr Gln Asn Ala    (SEQ ID NO:5)

Ala Phe Gly Lys Pro Ile Ile Lys Ala Ala Ser Met Tyr Asn Asn

Asp Ser Asn Val Arg Arg Ala Gln Asn Asp His Phe Leu Leu Gly

Gly His Asp Gly Tyr Arg Ile Leu Cys Ala Pro Val Val Trp Glu
```

-continued

Asn Ser Thr Glu Arg Glu Leu Tyr Leu Pro Val Leu Thr Gln Trp

Tyr Lys Phe Gly Pro Asp Phe Asp Thr Lys Pro Leu Glu Gly Ala

The Amino acid sequence (27–34) used to generate primer A and B
(Met Tyr Asn Asn Asp Ser Asn Val) (SEQ ID NO:21)

Primer A

ATG TA(TC) AA(CT) AA(CT) GA(CT) TC(GATC) AA(CT) GT             (SEQ ID NO:6) 128 mix Primer B ATG TA(TC) AA(CT) AA(CT) GA(CT) AG(CT) AA(CT) GT               (SEQ ID NO:7) 64 mix The Amino acid sequence (45–50) used to generate primer C
(Gly Gly His Asp Gly Tyr) (SEQ ID NO:22)

Primer C

TA (GATC)CC (GA)TC (GA)TG (GATC)CC (GATC)CC                    (SEQ ID NO:8) 256 mix

[The sequence corresponds to the complementary strand.]

The Amino acid sequence (74–79) used to generate primer
E (Gln Trp Tyr Lys Phe Gly) (SEQ ID No: 23)

Primer E

GG(GATC) CC(GA) AA(CT) TT(GA) TAC CA(CT) TG                    (SEQ ID NO:9) 64 mix

[The sequence corresponds to the complementary strand.]

The Amino acid sequence (1–6) used to generate primer F1 and F2
(Tyr Arg Trp Gln Glu Val) (SEQ ID NO:24)

Primer F1

TA(TC) CG(GATC) TGG CA(GA) GA(GA) GT                           (SEQ ID NO:10) 32 mix Primer F2

TA(TC) AG(GA) TGG CA(GA) GA(GA) GT                             (SEQ ID NO:11) 16 mix The sequence obtained from the first PCR amplification (clone 1)

ATGTACAACA ACGACTCGAA CGTTCGCAGG GCGCAGAACG ATCATTTCCT         (SEQ ID NO:12)

TCTTGGCGGC CACGACGGTT A

Met Tyr Asn Asn Asp Ser Asn Val Arg Arg Ala Gln Asn Asp His Phe Leu Leu Gly   (SEQ ID NO:13)

Gly His Asp Gly

The sequence obtained from the second PCR amplification (clone 1)

ATGTACAACA ACGACTCGAA CGTTCGCAGG GCGCAGAACG ATCATTTCCT         (SEQ ID NO:14)

TCTTGGTGGA CATGATGGAT ATCGCATTCT GTGCGCGCCT GTTGTGTGGG

AGAATTCGAC CGAACGNGAA TTGTACTTGC CCGTGCTGAC CCAATGGTAC

AAATTCGGCC C

Met Tyr Asn Asn Asp Ser Asn Val Arg Arg Ala Gln Asn Asp His Phe Leu Leu Gly   (SEQ ID NO:15)

Gly His Asp Gly Tyr Arg Ile Leu Cys Ala Pro Val Val Trp Glu Asn Ser Thr Glu

Arg Glu Leu Tyr Leu Pro Val Leu Thr Gln Trp Tyr Lys Phe Gly Pro

The sequence obtained from the third PCR amplification (clone2)

TACAGGTGGC AGGAGGTGTT GTACACTGCT ATGTACCAGA                    (SEQ ID NO:16)

ATGCGGCTTT CGGGAAACCG ATTATCAAGG CAGCTTCCAT

```
GTACGACAAC GACAGAAACG TTCGCGGCGC ACAGGATGAC

CACTTCCTTC TCGGCGGACA CGATGGATAT CGTATTTTGT

GTGCACCTGT TGTGTGGGAG AATACAACCA GTCGCGATCT

GTACTTGCCT GTGCTGACCA GTGGTACAAA TTCGGCCC
```

Tyr Arg Trp Gln Glu Val Leu Tyr Thr Ala Met Tyr Gln Asn Ala Ala Phe Gly Lys          (SEQ ID NO:17)

Pro Ile Ile Lys Ala Ala Ser Met Tyr Asp Asn Asp Arg Asn Val Arg Gly Ala Gln Asp

Asp His Phe Leu Leu Gly Gly His Asp Gly Tyr Arg Ile Leu Cys Ala Pro Val Val

Trp Glu Asn Thr Thr Ser Arg Asp Leu Tyr Leu Pro Val Leu Thr Lys Trp Tyr Lys

Phe Gly

1. Cytological Investigations of *Gracilariopsis lemaneiformis*

1.1.1 Detection of fungal infection in *Gracilariopsis lemaneiformis*

Sections of *Gracilariopsis lemaneiformis* collected in China were either hand cut or cut from paraffin embedded material. Sectioned material was carefully investigated by light microscopy. Fungal hyphae were clearly detected in *Gracilariopsis lemaneiformis*.

The thalli of the *Gracilariopsis lemaneiformis* are composed of cells appearing in a highly ordered and almost symmetric manner. The tubular thallus of *G. lemaneiformis* is composed of large, colourless central cells surrounded by elongated, slender, ellyptical cells and small, round, red pigmented peripherial cells. All algal cell types are characterized by thick cell walls. Most of the fungal hyphae are found at the interphase between the central layer of large cells and the peripherial layer. These cells can clearly be distinguished from the algae cells as they are long and cylindrical. The growth of the hypha e is observed as irregularities between the highly ordered algae cells. The most frequent orientation of the hypha is along the main axis of the algal thallus. Side branches toward tie central and periphery are detected in some cases. The hypha can not be confused with the endo/epiphytic 2nd generation of the algae.

Calcofluor White is known to stain chitin and cellulose containing tissue. The reaction with chitin requires four covalently linked terminal n-acetyl glucosamine residues. It is generally accepted that cellulose is almost restricted to higher plants although it might occur in trace amounts in some algae. It is further known that chitin is absent in Gracilaria.

Calcofluor White was found to stain domains corresponding to fungi hyfa cell walls in sectioned *Gracilariopsis lemaneiformis* material.

Figure 1A:
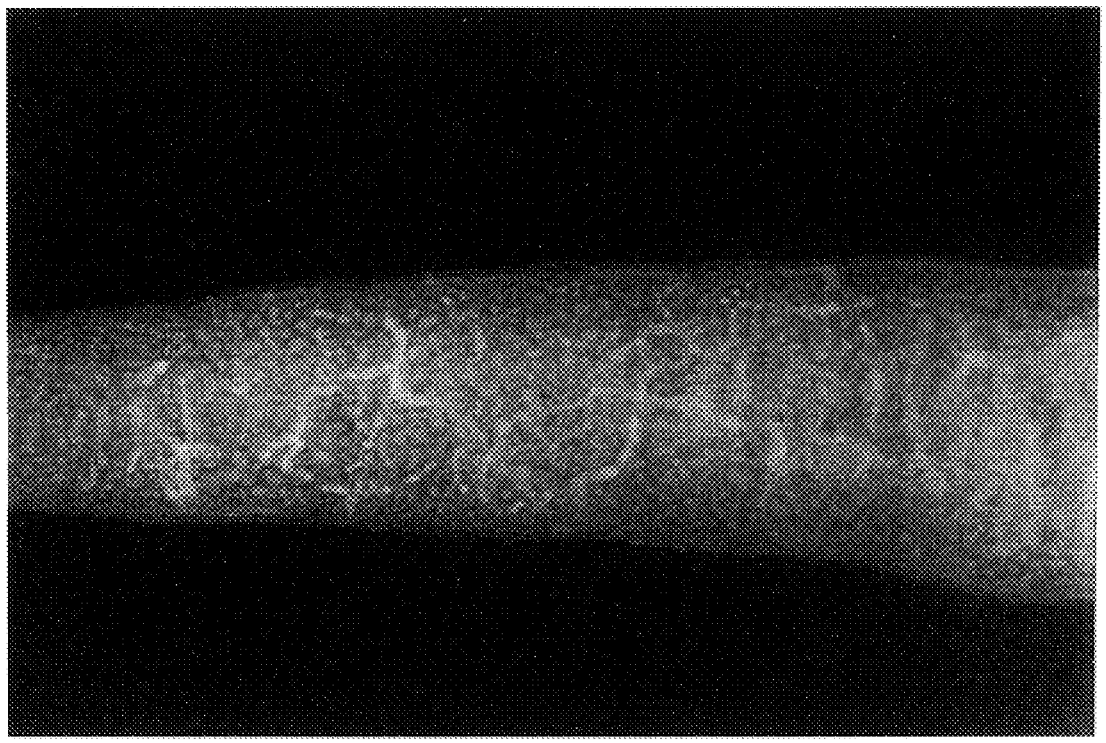
Figure 1B:
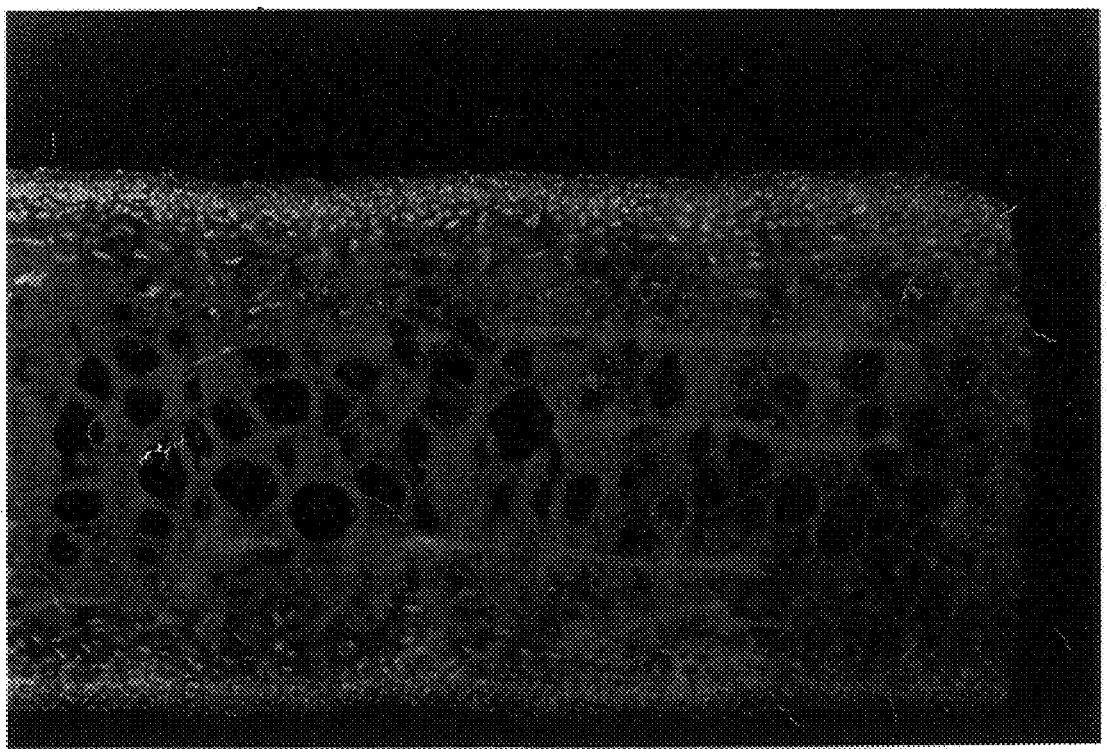

The hypha appear clear white against a faint blue background of Gracilaria tissue when observed under u.v. light—see FIGS. 1*a* and 1*b*. Chitin is the major cell wall component in most fungi but absent in Gracilaria. Based upon these observations we conclude that the investigated algae is infected by a fungi. 40% of the lower parts of the investigated *Gracilariopsis lemaneiformis* sections were found to be infected with fungal hyphae. In the algae tips 25% of the investigated *Gracilariopsis lemaneiformis* sections were found to be infected.

Figure 2:
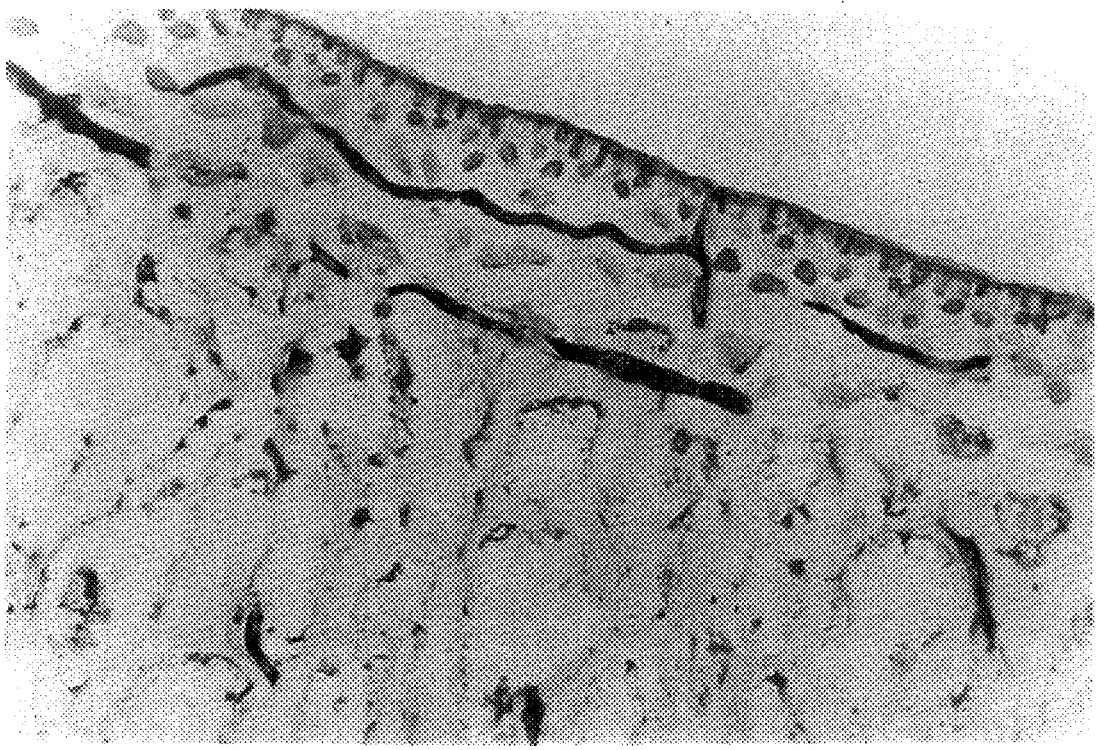
Figure 3A:
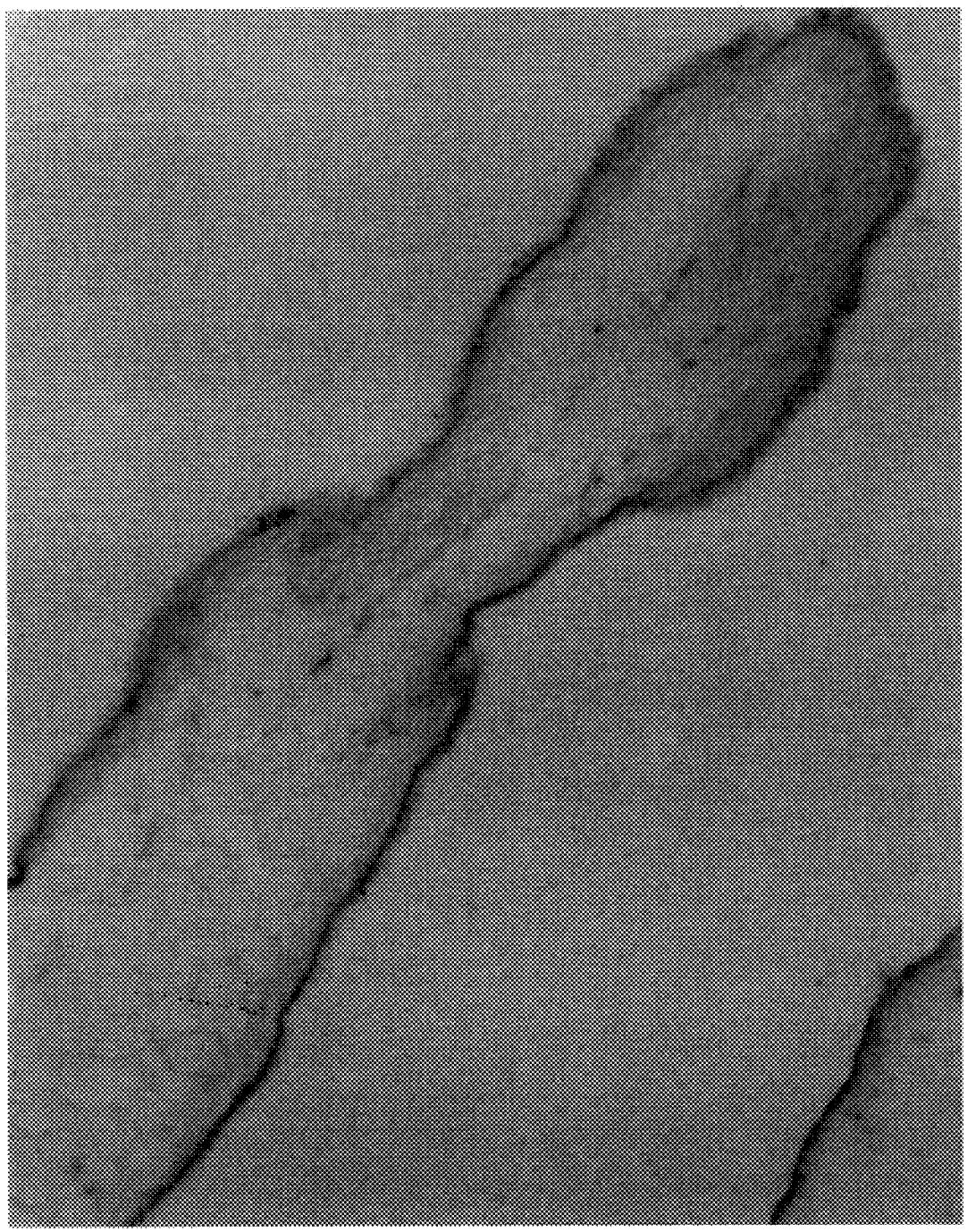
Figure 3B:
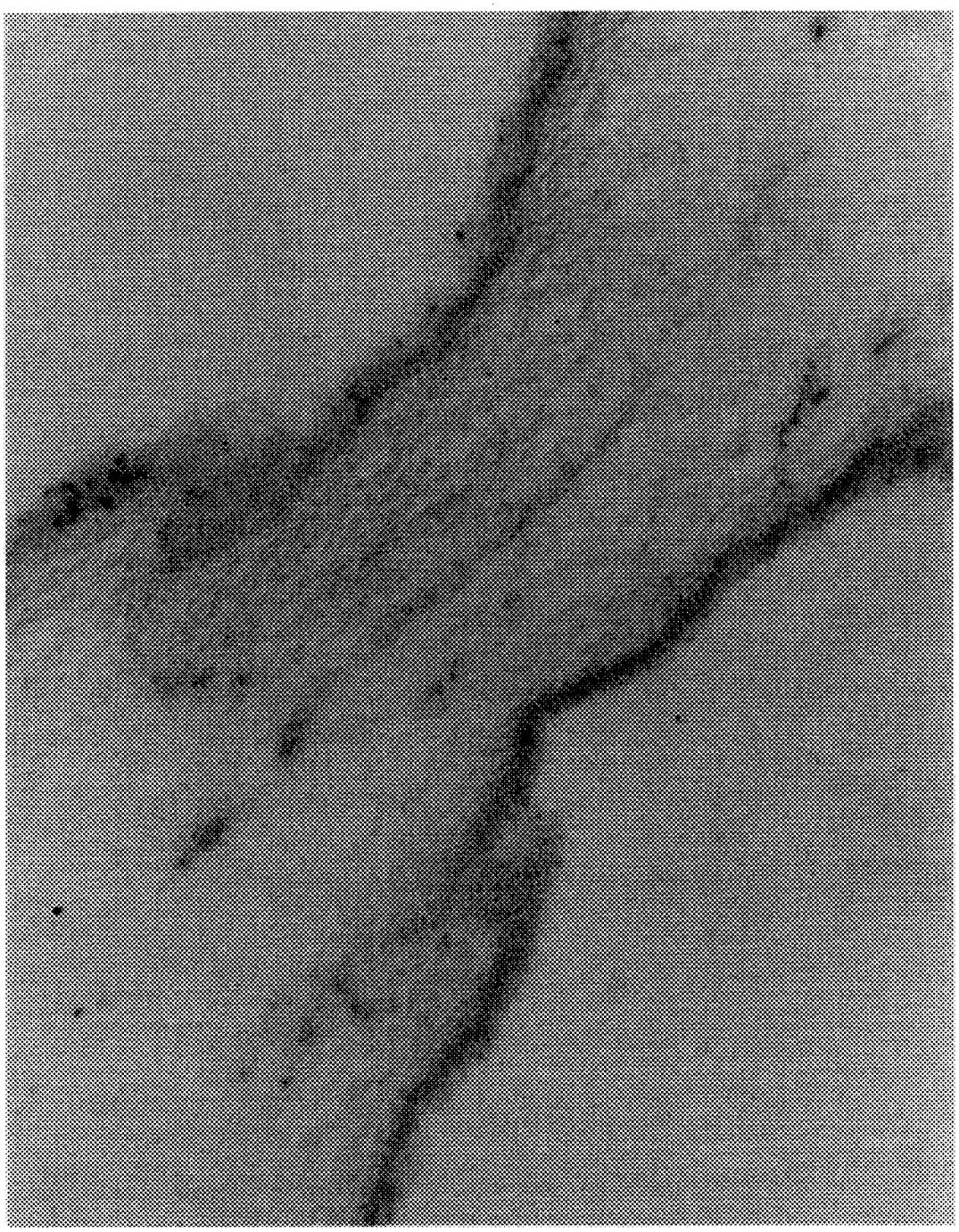
Figure 3C:
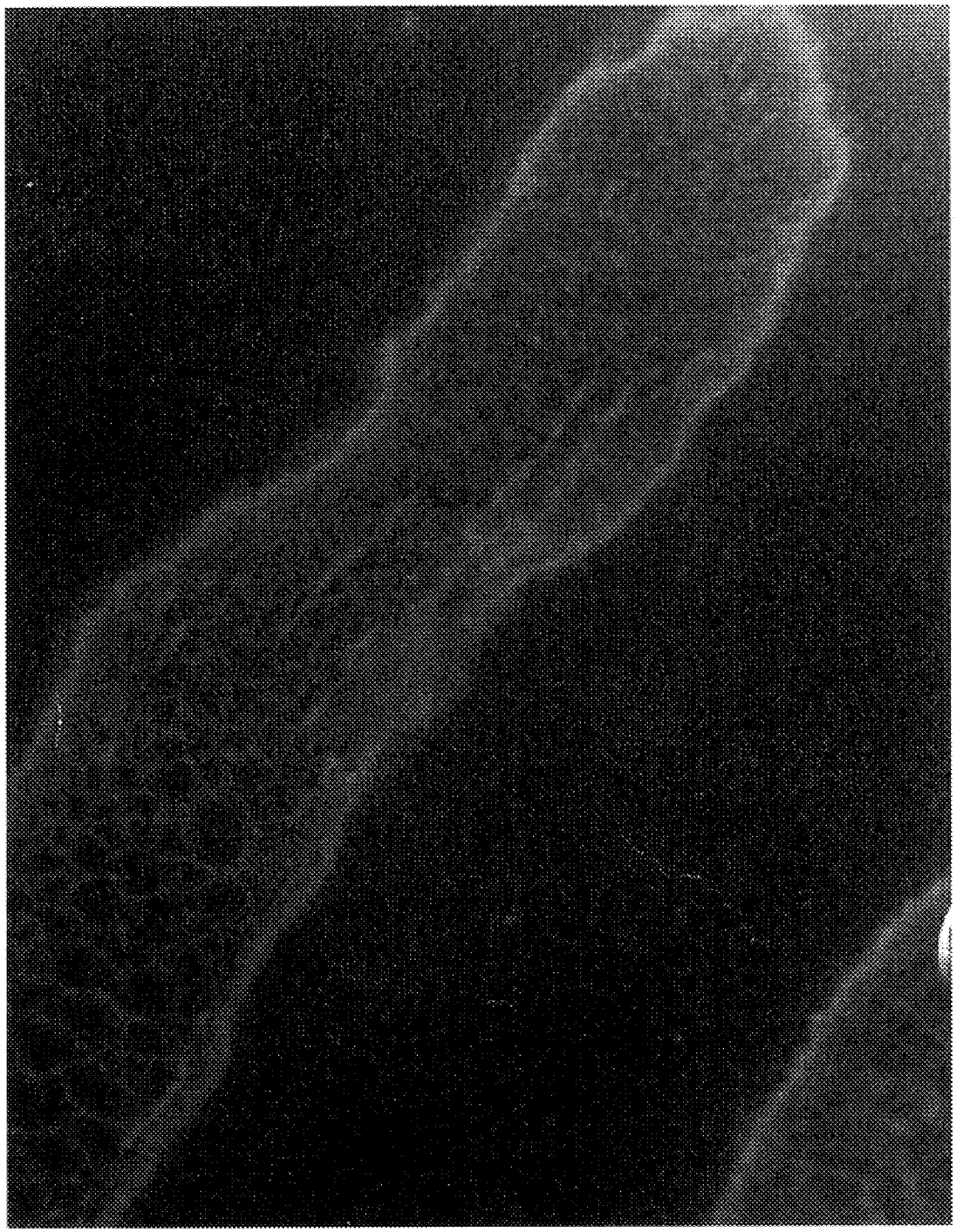
Figure 3D:
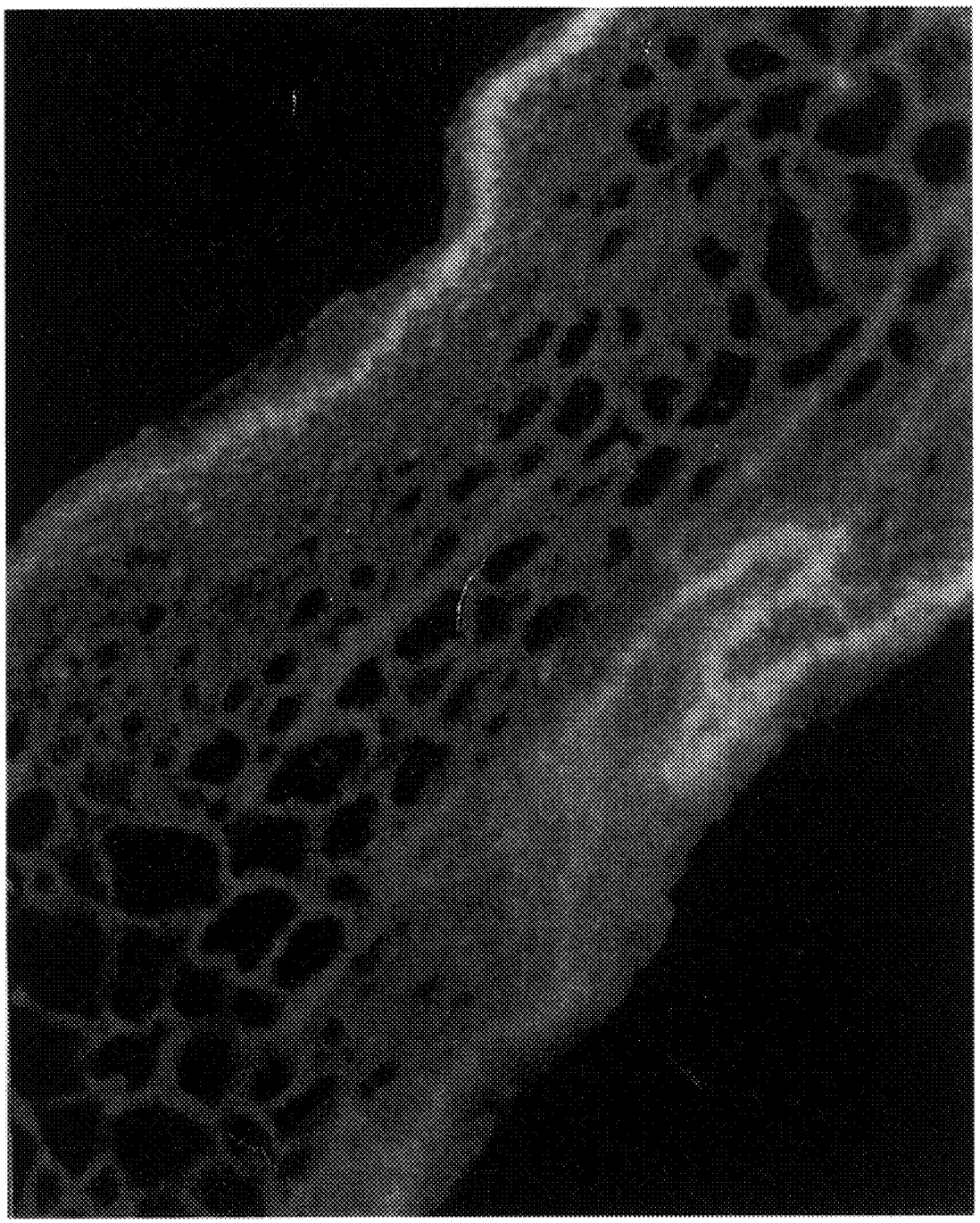
Figure 4:
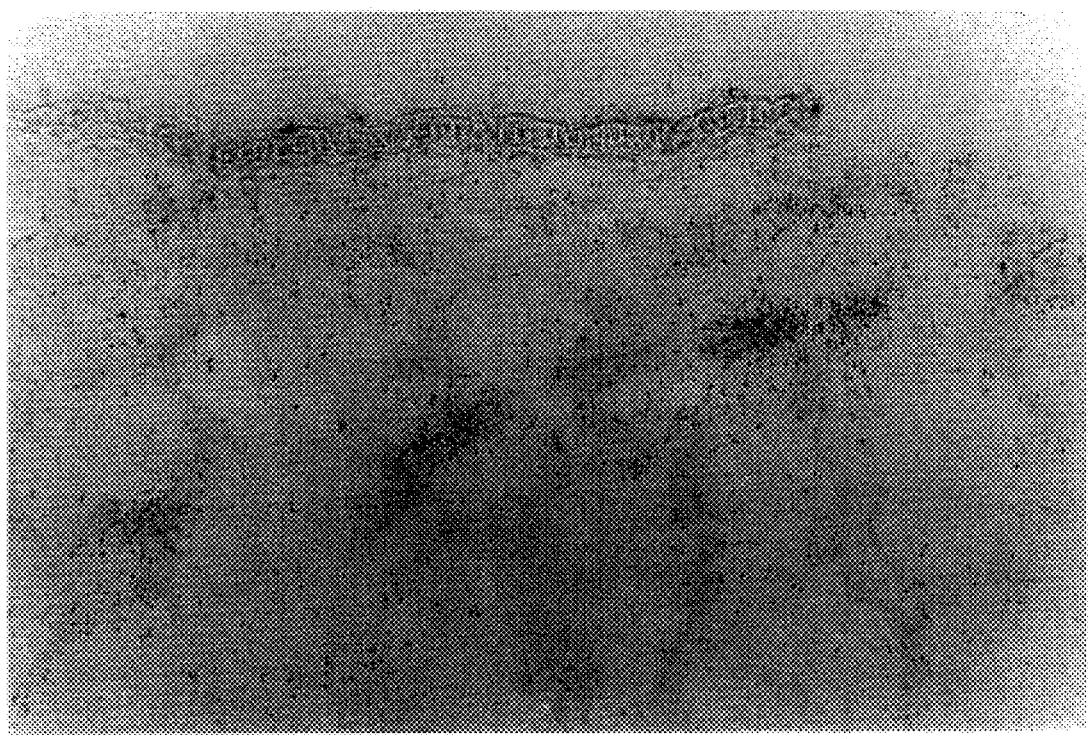
FIG. 4 shows intense antisense detections with clone 2 probe are found over the fungi in *Gracilariopsis lemaneiformis* (294×).
Figure 5:
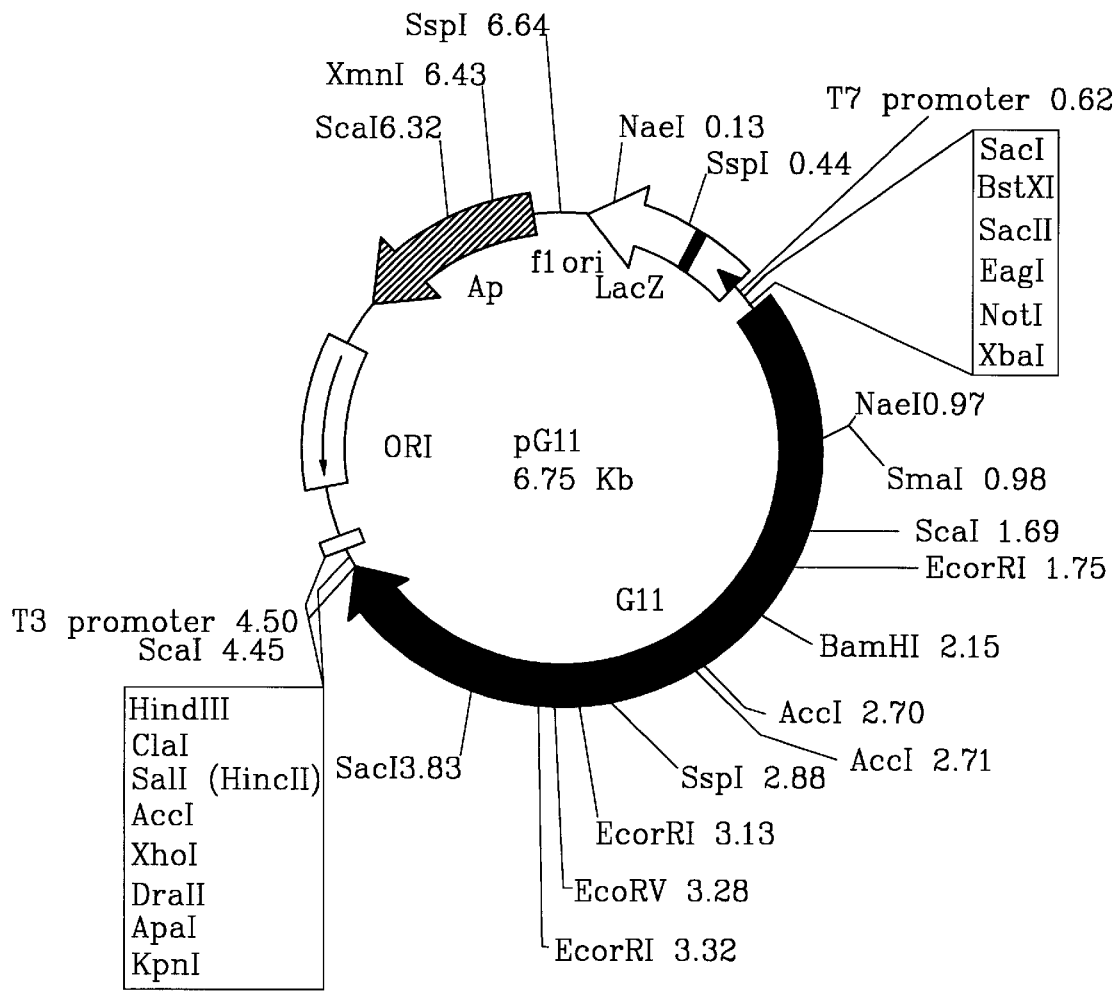
FIG. 5 shows a map of plasmid pGL1—which is a pBluescript II KS containing a 3.8 kb fragment isolated from a genomic library constructed from fungal infected *Gracilariopsis lemaneiformis*. The fragment contains a gene coding for alpha-1,4-glucan lyase.
Figure 6:
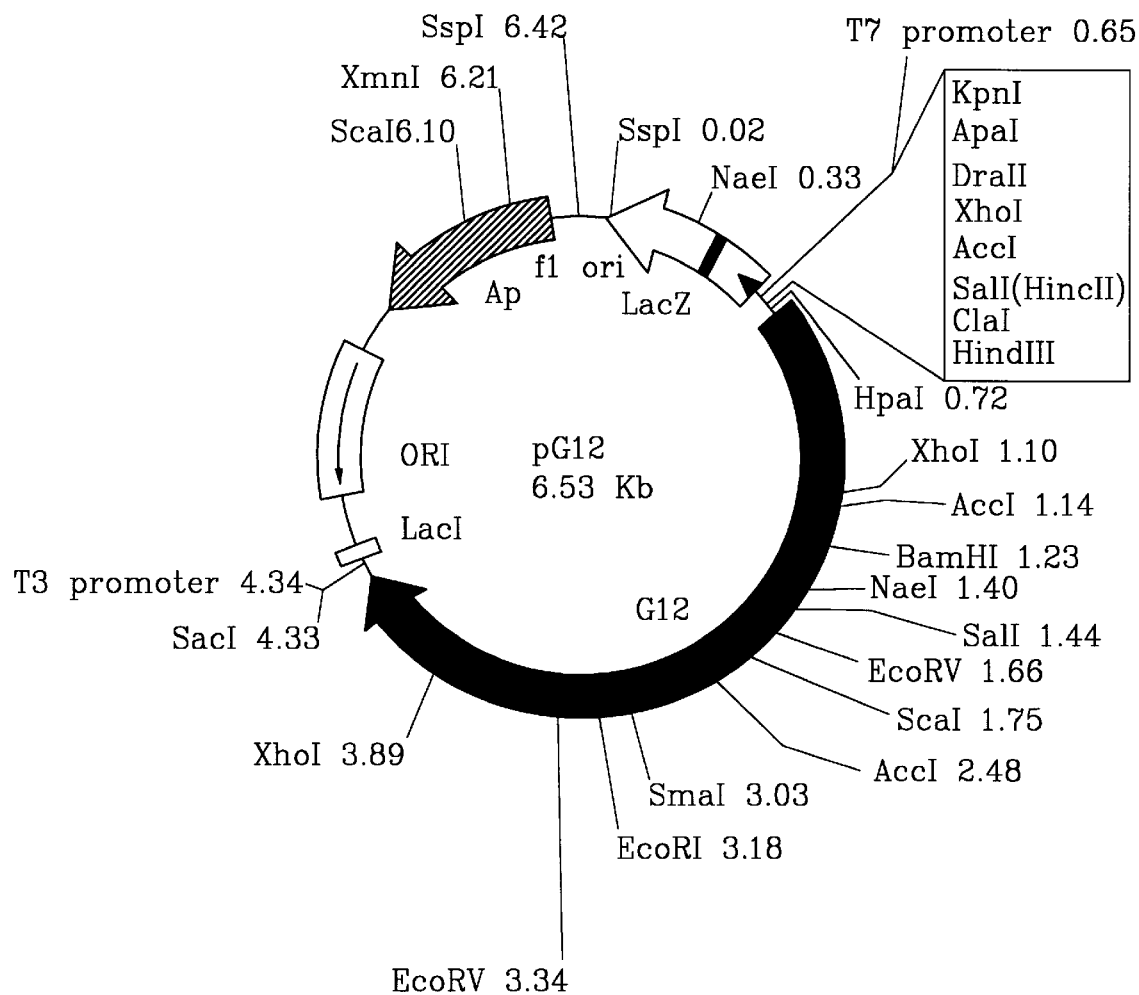
FIG. 6 shows a map of plasmid pGL2—which is a pBluescript II SK containing a 3.6 kb fragment isolated from a genomic library constructed from fungal infected *Gracilariopsis lemaneiformis*. The fragment contains a gene coding for alpha-1,4-glucan lyase.

Staining of sectioned *Gracilariopsis lemaneiformis* with Periodic acid Schiff (PAS) and Aniline blue black revealed a significantly higher content of carbohydrates within the fungal cells as compared with the algae cells—see FIG. 2. Safranin O and Malachit Green showed the same colour reaction of fungi cells as found in higher plants infected with fungi.

An Acridin Orange reaction with sectioned *Gracilariopsis lemaneiformis* showed clearly the irregularly growth of the fungus.

1.1.2 Electron Microscopy

Slides with 15 μm thick sections, where the fungus was detected with Calcofluor White were fixed in 2% $OsO_4$, washed in water and dehydrated in dimethoxypropane and absolute alcohol. A drop of a 1:1 mixture of acetone and Spurr resin was placed over each section on the glass slide, and after one hour replaced by a drop of pure resin. A gelatin embedding capsule filled with resin was placed face down over the section and left over night at 4° C. After the polymerization at 55° C. for 8 hrs, the thick sections adhering to the resin blocks could can be separated from the slide by immersion in liquid nitrogen.

Blocks were trimmed and 100 nm thick sections were cut using a diamond knife on a microtome. The sections were stained in aqueous uranyl acetate and in lead citrate. The sections were examined in an electron microscope at 80 kV.

The investigation confirmed the light microscopical observations and provided further evidence that the lyase producing, chinese strain of *G. lamneiformis* is infected by a fungal parasite or symbiont.

Fungal hyphae are build of tubular cells 50 to 100 μm long and only few microns in diameter. The cells are serially arranged with septate walls between the adjacent cells. Ocasional branches are also seen. The hyphae grow between the thick cell walls of algal thallus without penetrating the wall or damaging the cell. Such a symbiotic association, called mycophycobiosis, is known to occur between some filamentous marine fungi and large marine algae (Donk and Bruning, 1992—Ecology of aquatic fungi in and on algae. In Reisser, W.(ed.): Algae and Symbioses: Plants, Animals, Fungi, Viruses, Interactions Explored. Biopress Ltd., Bristol.)

Examining the microphotograph in FIG. 9, several differences between algal and fungal cells can be noticed. In contrast to several μm thick walls of the alga, the fungal walls are only 100–200 nm thick. Plant typical organells as chloroplasts with thyllacoid membranes as well as floridean starch grains can be seen in algal cells, but not in the fungus.

Intercellular connections of red algae are characterized by specific structures termed pit plugs, or pit connections The structures are prominent, electron dense cores and they are important features in algal taxonomy (Pueschel, C. M.: An expanded survey of the ultrastructure of Red algal pit plugs. J. Phycol. 25, 625, (1989)). In our material, such connections were frequently observed in the algal thallus, but never between the cells of the fungus.

1.2 In situ Hybridization Experiments

In situ hybridization technique is based upon the principle of hybridization of an antisense ribonucotide sequence to the mRNA. The technique is used to visualize areas in microscopic sections where said mRNA is present. In this particular case the technique is used to localize the enzyme α-1,4-glucan lyase in sections of *Gracilariopsis lemaneiformis*.

1.2.1 Preparation of $^{35}$S Labelled Probes for In situ Hybridization

A 238 bp PCR fragment from a third PCR amplification—called clone 2 (see above)—was cloned into the pGEM-3Zf (+) Vector (Promega). The transcription of the antisense RNA was driven by the SP6 promotor, and the sense RNA by the T7 promotor. The Ribonuclease protection assay kit (Ambion) was used with the following modifications. The transcripts were run on a 6% sequencing gel to remove the unincorporated nucleotide and eluted with the elution buffer supplied with the T7RNA polymerase in vitro Transcription Kit (Ambion). The antisense transcript contained 23 non-coding nucleotides while the sense contained 39. For hybridization $10^7$ cpm/ml of the $^{35}$S labelled probe was used.

In situ hybridisation was performed essentially as described by Langedale et.al.(1988). The hybridization temperature was found to be optimal at 45° C. After washing at 45° C. the sections were covered with KodaK K-5 photographic emulsion and left for 3 days at 5° C. in dark (Ref: Langedale, J. A., Rothermel, B. A. and Nelson, T. (1988). Genes and development 2: 106–115. Cold Spring Harbour Laboratory).

The in situ hybridization experiments with riboprobes against the mRNA of α-1,4-glucan lyase, show strong hybridizations over and around the hypha of the fungus detected in *Gracilariopsis lemaneiformis*—see FIGS. 3a–d and 4. This is considered a strong indication that the α-1,4-glucan lyase is produced. A weak random background reactions were detected in the algae tissue of both *Gracilariopsis lemaneiformis*. This reaction was observed both with the sense and the antisense probes. Intense staining over the fungi hypha was only obtained with antisense probes.

These results were obtained with standard hybridisation conditions at 45° C. in hybridization and washing steps. At 50° C. no staining over the fungi was observed, whereas the background staining remained the same. Raising the temperature to 55° C. reduced the background staining with both sense and antisense probes significantly and equally.

Based upon the cytological investigations using complementary staining procedures it is concluded that *Gracilariopsis lemaneiformis* is fungus infected. The infections are most pronounced in the lower parts of the algal tissue.

In sectioned *Gracilariopsis lemaneiformis* material in situ hybridization results clearly indicate that hybridization is restricted to areas where fungal infections are found—see FIGS. 3a–d. The results indicate that α-1,4-glucan lyase mRNA appears to be restricted to fungus infected areas in *Gracilariopsis lemaneiformis*.

Based upon these observations we conclude that α-1,4-glucan lyase activity is detected in fungally infected *Gracilariopsis lemaneiformis*.

2. Enzyme Purification and Characterization

Purification of α-1,4-glucan lyase from fungal infected *Gracilariopsis lemaneiformis* material was performed as follows.

2.1 Materials and Methods

The algae were harvested by filtration and washed with 0.9% NaCl. The cells were broken by homogenization followed by sonication on ice for 6×3 min in 50 mM citrate-NaOH pH 6.2 (Buffer A). Cell debris were removed by centrifugation at 25,000×g for 40 min. The supernatant obtained at this procedure was regarded as cell-free extract and was used for activity staining and Western blotting after separation on 8–25% gradient gels.

2.2 Separation by β-cyclodextrin Sepharose gel

The cell-free extract was applied directly to a β-cyclodextrin Sepharose gel 4B column ( 2.6×18 cm) pre equilibrated with Buffer A. The column was washed with 3 volumes of Buffer A and 2 volumes of Buffer A containing 1 M NaCl. α1,4-glucan lyase was eluted with 2% dextrins in Buffer A. Active fractions were pooled and the buffer changed to 20 mM Bis-tris propane-HCl (pH 7.0, Buffer B).

Active fractions were applied onto a Mono Q HR 5/5 column pre-equilibrated with Buffer B. The fungal lyase was eluted with Buffer B in a linear gradient of 0.3 M NaCl.

The lyase preparation obtained after, β-cyclodextrin Sepharose chromatography was alternatively concentrated to 150 µl and applied on a Superose 12 column operated under FPLC conditions.

2.3 Assay for α-1,4-glucan lyase activity and conditions for determination of substrate specificity, pH and temperature optimum The reaction mixture for the assay of the α-1,4-glucan lyase activity contained 10 mg ml$^{-1}$ amylopectin and 25 mM Mes-NaOH (pH 6.0). The reaction was carried out at 30° C. for 30 min and stopped by the addition of 3,5-dinitrosalicylic acid reagent. Optical density at 550 nm was measured after standing at room temperature for 10 min.

3. Amino Acid Sequencing of the α-1,4-Glucan Lyase from Fungus Infected Gracilariopsis Lemaneiformis 3.1 Amino Acid Sequencing of the Lyases The lyases were digested with either endoproteinase Arg-C from *Clostridium histolyticum* or endoproteinase Lys-C from *Lysobacter enzymogenes*, both sequencing grade purchased from Boehringer Mannheim, Germany. For digestion with endoproteinase Arg-C, freeze dried lyase (0.1 mg) was dissolved in 50 µl 10 M urea, 50 mM methylamine, 0.1 M Tris-HCl, pH 7.6. After overlay with $N_2$ and addition of 10 µl of 50 mM DTT and 5 mM EDTA the protein was denatured and reduced for 10 min at 50° C. under $N_2$. Subsequently, 1 µg of endoproteinase Arg-C in 10 µl of 50 mM Tris-HCl, pH 8.0 was added, $N_2$ was overlayed and the digestion was carried out for 6 h at 37° C. For subsequent cysteine derivatization, 12.5 µl 100 mM iodoacetamide was added and the solution was incubated for 15 min at RT in the dark under $N_2$.

For digestion with endoproteinase Lys-C, freeze dried lyase (0.1 mg) was dissolved in 50 µof 8 M urea, 0.4 M $NH_4HCO_3$, pH 8.4. After overlay with $N_2$ and addition of 5 µl of 45 mM DTT, the protein was denatured and reduced for 15 min at 50° C. under $N_2$. After cooling to RT, 5 µl of 100 mM iodoacetamide was added for the cysteines to be derivatized for 15 min at RT in the dark under $N_2$.

Subsequently, 90 µl of water and 5 µg of endoproteinase Lys-C in 50 µl of 50 mM tricine and 10 mM EDTA, pH 8.0, was added and the digestion was carried out for 24 h at 37° C. under $N_2$.

The resulting peptides were separated by reversed phase HPLC on a VYDAC C18 column (0.46×15 cm; 10 µm; The Separations Group; California) using solvent A: 0.1% TFA in water and solvent B: 0. 1% TFA in acetonitrile. Selected peptides were rechromatographed on a Develosil C18 column (0.46×10 cm; 3 µm; Dr. Ole Schou, Novo Nordisk, Denmark) using the same solvent system prior to sequencing on an Applied Biosystems 476A sequencer using pulsed-liquid fast cycles.

The amino acid sequence information from the enzyme derived from fungus infected *Gracilariopsis lemaneiformis* is shown below, in particular SEQ. ID. No. 1. and SEQ. ID. No. 2.

SEQ. I.D. No. 1 has:
Number of residues: 1088.
Amino acid composition (including the signal sequence)

61 Ala    15 Cys    19 His    34 Met    78 Thr

51 Arg    42 Gln    43 Ile    53 Phe    24 Trp

88 Asn    53 Glu    63 Leu    51 Pro    58 Tyr

79 Asp   100 Gly    37 Lys    62 Ser    77 Val

SEQ. I.D. No. 2 has:
Number of residues: 1091.
Amino acid composition (including the signal sequence)

58 Ala    16 Cys    14 His    34 Met    68 Thr

57 Arg    40 Gln    44 Ile    56 Phe    23 Trp

84 Asn    47 Glu    69 Leu    51 Pro    61 Tyr

81 Asp   102 Gly    50 Lys    60 Ser    76 Val 3.2 N-terminal Analysis

Studies showed that the N-terminal sequence of native glucan lyase 1 was blocked. Deblocking was achieved by treating glucan lyase 1 blotted onto a PVDF membrane with anhydrous TFA for 30 min at 40° C. essentially as described by LeGendre et al. (1993) [Purification of proteins and peptides by SDS-PAGE; In: Matsudaira, P. (ed.) A practical guide to protein and peptide purification for microsequencing, 2nd edition; Academic Press Inc., San Diego; pp. 74–101.]. The sequence obtained was TALSD-KQTA (SEQ ID NO:25), which matches the sequence (sequence position from 51 to 59 of SEQ. I.D. No.1) derived from the clone for glucan lyase 1 and indicates N-acetylthreonine as N-terminal residue of glucan lyase 1. Sequence position 1 to 50 of SEQ. I.D. No. 1 represents a signal sequence.

4. DNA Sequencing of Genes Coding for the α-1,4-Glucan Lyase from Fungus Infected Gracilariopsis lemaneiformis 4.1 Methods for Molecular Biology DNA was isolated as described by Saunders (1993) with the following modification: The polysaccharides were removed from the DNA by ELUTIP-d (Schleicher & Schuell) purification instead of gel purification. (Ref: Saunders, G. W. (1993). Gel purification of red algal genomic DNA: An inexpensive and rapid method for the isolation of PCR-friendly DNA. Journal of phycology 29(2): 251–254 and Schleicher & Schuell: ELUTIP-d. Rapid Method for Purification and Concentration of DNA.)

4.2 PCR

The preparation of the relevant DNA molecule was done by use of the Gene Amp DNA Amplification Kit (Perkin Elmer Cetus, USA) and in accordance with the manufactures instructions except that the Taq polymerase was added later (see PCR cycles) and the temperature cycling was changed to the following:

| PCR cycles: | | |
|---|---|---|
| no of cycles | C | time (min.) |
| 1 | 98 | 5 |
|  | 60 | 5 |

-continued

| PCR cycles: | | |
|---|---|---|
| no of cycles | C | time (min.) |
| addition of Taq polymerase and oil | | |
| 35 | 94 | 1 |
|  | 47 | 2 |
|  | 72 | 3 |
| 1 | 72 | 20 |

4.3 Cloning of PCR Fragments

PCR fragments were cloned into pT7Blue (from Novagen) following the instructions of the supplier.

4.4 DNA Sequencing

Double stranded DNA was sequenced essentially according to the dideoxy method of Sanger et al. (1979) using the Auto Read Sequencing Kit (Pharmacia) and the Pharmacia LKB A.L.F.DNA sequencer. (Ref: Sanger, F., Nicklen, S. and Coulson, A. R.(1979). DNA sequencing with chain-determinating inhibitors. Proc. Natl. Acad. Sci. USA 74: 5463–5467.).

The sequences are shown as SEQ. I.D. No.s 3 and 4, wherein

SEQ. I.D. No. 3 has:
Total number of bases is: 3267.
DNA sequence composition: 850 A; 761 C; 871 G; 785 T
SEQ. I.D. No. 4 has:
Total number of bases is: 3276.
DNA sequence composition: 889 A; 702 C; 856 G; 829 T 4.5 Screening of the Library Screening of the Lambda Zap library obtained from Stratagene, was performed in accordance with the manufacturer's instructions except that the prehybridization and hybridization was performed in 2×SSC, 0.1% SDS, 10×Denhardt's and 100 μg/ml denatured salmon sperm DNA. To the hybridization solution a 32P-labeled denatured probe was added. Hybridization was performed over night at 55° C. The filters were washed twice in 2×SSC, 0.1% SDS and twice in 1×SSC, 0.1% SDS.

4.6 Probe

The cloned PCR fragments were isolated from the pT7 blue vector by digestion with appropriate restriction enzymes. The fragments were separated from the vector by agarose gel electrophoresis and the fragments were purified from the agarose by Agarase (Boehringer Mannheim). As the fragments were only 90–240 bp long the isolated fragments were exposed to a ligation reaction before labelling with 32P-dCTP using either Prime-It random primer kit (Stratagene) or Ready to Go DNA labelling kit (Pharmacia).

4.7 Results 4.7.1 Generation of PCR DNA fragments coding for α-1,4-glucan lyase.

The amino acid sequences of three overlapping tryptic peptides from α-1,4-glucan lyase were used to generate mixed oligonucleotides, which could be used as PCR primers (see the sequences given above).

In the first PCR amplification primers A/B (see above) were used as upstream primers and primer C (see above) was used as downstream primer. The size of the expected PCR product was 71 base pairs.

In the second PCR amplification primers A/B were used as upstream primers and E was used as downstream primer. The size of the expected PCR product was 161 base pairs.

In the third PCR amplification primers F1 (see above) and F2 (see above) were used as upstream primers and E was used as downstream primer. The size of the expected PCR product was 238 base pairs. The PCR products were analysed on a 2% LMT agarose gel and fragments of the expected sizes were cut out from the gel and treated with Agarase (Boehringer Manheim) and cloned into the pT7blue Vector (Novagen) and sequenced.

The cloned fragments from the first and second PCR amplification coded for amino acids corresponding to the sequenced peptides (see above). The clone from the third amplification (see above) was only about 87% homologous to the sequenced peptides.

4.7.2 Screening of the Genomic Library with the Cloned PCR Fragments

Screening of the library with the above-mentioned clones gave two clones. One clone contained the nucleotide sequence of SEQ I.D. No. 4 (gene 2). The other clone contained some of the sequence of SEQ I.D. No.3 (from base pair 1065 downwards) (gene 1).

The 5' end of SEQ. I.D. No. 3 (i.e. from base pair 1064 upwards) was obtained by the RACE (rapid amplification of cDNA ends) procedure (Michael, A. F., Michael, K. D. & Martin, G. R.(1988). Proc. Natl. Acad. Sci. USA 85: 8998–99002.) using the 5' race system from Gibco BRL. Total RNA was isolated according to Collinge et al. (Collinge, D. B., Milligan D. E:, Dow, J. M., Scofield, G. & Daniels, M. J.(1987). Plant Mol Biol 8: 405–414). The 5' race was done according to the protocol of the manufacturer, using 1 μg of total RNA. The PCR product from the second amplification was cloned into pT7blue vector from Novagen according to the protocol of the manufacturer. Three independent PCR clones were sequenced to compensate for PCR errors.

An additional PCR was performed to supplement the clone just described with XbaI and NdeI restriction sites immediately in front of the ATG start codon using the following oligonucleotide as an upstream primer: GCTCTA-GAGCATGTTTTCAACCCTTGCG (SEQ ID No:18) and a primer containing the complement sequence of bp 1573–1593 in sequence GL1 (i.e. SEQ. I.D. No. 3) was used as a downstream primer.

The complete sequence for gene 1 (i.e. SEQ. I.D. No. 3) was generated by cloning the 3' end of the gene as a BamHI-HindIII fragment from the genomic clone into the pBluescript II KS+ vector from Stratagene and additionally cloning the PCR generated 5' end of the gene as a XbaI-BamHI fragment in front of the 3' end.

Gene 2 was cloned as a HindIII blunt ended fragment into the EcoRV site of pBluescript II SK+ vector from Stratagene. A part of the 3' untranslated sequence was removed by a SacI digestion, followed by religation. HindIII and HpaI restriction sites were introduced immediately in front of the start ATG by digestion with HindIII and NarI and religation in the presence of the following annealed oligonucleotides

```
                      (SEQ ID NO:19)
AGCTTGTTAACATGTATCCAACCCTCACCTTCGTGG (SEQ ID NO:20)
    ACAATTGTACATAGGTTGGGAGTGGAAGCACCGC
```

No introns were found in the clones sequenced.

The clone 1 type (SEQ.ID.No.3) can be aligned with all ten peptide sequences (see FIG. 8) showing 100% identity. Alignment of the two protein sequences encoded by the genes isolated from the fungal infected algae *Gracilariopsis lemaneiformis* shows about 78% identity, indicating that both genes are coding for a α-1.4-glucan lyase.

5. Expression of the GL Gene in Micro-Organisms (E.G. Analyses of Pichia Lyase Transformants and Aspergillus Lyase Transformants)

The DNA sequence encoding the GL was introduced into microorganisms to produce an enzyme with high specific activity and in large quantities.

In this regard, gene 1 (i.e. SEQ. I.D. No. 3) was cloned as a NotI-HindIII blunt ended (using the DNA blunting kit from Amersham International) fragment into the Pichia expression vector pHIL-D2 (containing the AOX1 promoter) digested with EcoRI and blunt ended (using the DNA blunting kit from Amersham International) for expression in *Pichia pastoris* (according to the protocol stated in the Pichia Expression Kit supplied by Invitrogen).

In another embodiment, the gene 1 (i.e. SEQ. I.D. No. 3) was cloned as a NotI-HindIII blunt ended fragment (using the DNA blunting kit from Amersham International) into the Aspergillus expression vector pBARMTE1 (containing the methyl tryptophan resistance promoter from *Neuropera crassa*) digested with SmaI for expression in *Aspergillus niger* (Pall et al (1993) Fungal Genet Newslett. vol 40 pages 59–62). The protoplasts were prepared according to Daboussi et al (Curr Genet (1989) vol 15 pp 453–456) using lysing enzymes Sigma L-2773 and the lyticase Sigma L-8012. The transformation of the protoplasts was followed according to the protocol stated by Buxton et al (Gene (1985) vol 37 pp 207–214) except that for plating the transformed protoplasts the protocol laid out in Punt et al (Methods in Enzymology (1992) vol 216 pp 447–457) was followed but with the use of 0.6% osmotic stabilised top agarose.

The results showed that lyase activity was observed in the transformed *Pichia pastoris* and *Aspergillus niger*.

5.1 General Methods

Preparation of cell-free extracts.

The cells were harvested by centrifugation at 9000 rpm for 5 min and washed with 0.9% NaCl and resuspended in the breaking buffer (5 mM K-phosphate, pH 7.5 containing 1 mM of EDTA, and 5% glycerol). Cells were broken using glass beads and vortex treatment. The breaking buffer contained 1 mM PMSF (protease inhibitor). The lyase extract (supernatant) was obtained after centrifugation at 9000 rpm for 5 min followed by centrifugation at 20,000×g for 5 min.

Assay of lyase activity by alkaline 3,5-dinitrosalicylic acid reagent (DNS) One volume of lyase extract was mixed with an equal volume of 4% amylopectin solution. The reaction mixture was then incubated at a controlled temperature and samples were removed at specified intervals and analyzed for AF.

The lyase activity was also analyzed using a radioactive method.

The reaction mixture contained 10 μl $^{14}$C-starch solution (1 μCi; Sigma Chemicals Co.) and 10 μl of the lyase extract. The reaction mixture was left at 25° C. overnight and was then analyzed in the usual TLC system. The radioactive AF produced was detected using an Instant Imager (Pachard Instrument Co., Inc., Meriden, Conn.).

Electrophoresis and Western blotting

SDS-PAGE was performed using 8–25% gradient gels and the PhastSystem (Pharmacia). Western blottings was also run on a Semidry transfer unit of the PhastSystem.

Primary antibodies raised against the lyase purified from the red seaweed collected at Qingdao (China) were used in a dilution of 1:100. Pig antirabbit IgG conjugated to alkaine phosphatase (Dako A/S, Glostrup, Denmark) were used as secondary antibodies and used in a dilution of 1:1000.

Part I, Analysis of the Pichia Transformants Containing the above Mentioned Construct Results 1. Lyase activity was determined 5 days after induction (according to the manual) and proved the activity to be intracellular for all samples in the B series.

| Samples of B series: | 11 | 12 | 13 | 15 | 26 | 27 | 28 | 29 | 30 |
|---|---|---|---|---|---|---|---|---|---|
| Specific activity: | 139 | 81 | 122 | 192 | 151 | 253 | 199 | 198 | 150 |

*Specific activity is defined as nmol AF released per min per mg protein in a reaction mixture containing 2% (w/v) of glycogen, 1% (w/v) glycerol in 10 mM potassium phosphate buffer (pH 7.5). The reaction temperature was 45° C.; the reaction time was 60 min.

A time course of sample B27 is as follows. The data are also presented in FIG. 1.

| Time (min) | 0 | 10 | 20 | 30 | 40 | 50 | 60 |
|---|---|---|---|---|---|---|---|
| Spec. act. | 0 | 18 | 54 | 90 | 147 | 179 | 253 |

Assay conditions were as above except that the time was varied.

2. Western-blotting analysis.

The CFE of all samples showed bands with a molecular weight corresponding to the native lyase.

| MC-Lyase expressed intracellularly in *Pichia pastoris* | |
|---|---|
| Names of culture | Specific activity* |
| A18 | 10 |
| A20 | 32 |
| A21 | 8 |
| A22 | 8 |
| A24 | 6 |

Part II, The Aspergilus Transformants

Results

I. Lyase activity was determined after 5 days incubation (minimal medium containing 0.2% casein enzymatic hydrolysate analysis by the alkaline 3,5-dinitrosalicylic acid reagent 1). Lyase activity analysis of the culture medium Among 35 cultures grown with 0.2% amylopectin included in the culture medium, AF was only detectable in two cultures. The culture medium of 5.4+ and 5.9+ contained 0.13 g AF/liter and 0.44 g/liter, respectively. The result indicated that active lyase had been secreted from the cells. Lyase activity was also measurable in the cell-free extract.

2). Lyase activity analysis in cell-free extracts

| Name of the culture | Specific activity* |
|---|---|
| 5.4+ | 51 |
| 5.9+ | 148 |
| 5.13 | 99 |
| 5.15 | 25 |
| 5.19 | 37 |

*The specific activity was defined as nmol of AF produced per min per mg protein at 25° C. + indicates that 0.2% amylopectin was added.

The results show that Gene 1 of GL was expressed intracellular in *A. niger*.

Experiments with transformed *E.coli* (using cloning vectors pQE30 from the Qia express vector kit from Qiagen) showed expression of enzyme that was recognised by antibody to the enzyme purified from fungally infected *Gracilariopsis lemaneiformis*.

Instead of *Aspergillus niger* as host, other industrial important microorganisms for which good expression systems are known could be used such as: *Aspergillus oryzae*, Aspergillus sp., Trichoderma sp., *Saccharomyces cerevisiae*, Kluyveromyces sp., Hansenula sp., Pichia sp., *Bacillus subtilis, B. amyloliquefaciens*, Bacillus sp., Streptomyces sp. or *E. coli*.

Other preferred embodiments of the present invention include any one of the following: A transformed host organism having the capability of producing AF as a consequence of the introduction of a DNA sequence as herein described; such a transformed host organism which is a microorganism—preferably wherein the host organism is selected from the group consisting of bacteria, moulds, fungi and yeast; preferably the host organism is selected from the group consisting of Saccharomyces, Kluyveromyces, Aspergillus, Trichoderma Hansenula, Pichia, Bacillus Streptomyces, Eschericia such as *Aspergillus oryzae, Saccharomyces cerevisiae, bacillus sublilis, Bacillus amyloliquefascien, Eschericia coli.*; A method for preparing the sugar 1,5-D-anhydrofructose comprising contacting an alpha 1,4-glucan (e.g. starch) with the enzyme α-1,4-glucan lyase expressed by a transformed host organism comprising a nucleotide sequence encoding the same, preferably wherein the nucleotide sequence is a DNA sequence, preferably wherein the DNA sequence is one of the sequences hereinbefore described; A vector incorporating a nucleotide sequence as hereinbefore described, preferably wherein the vector is a replication vector, preferably wherein the vector is an expression vector containing the nucleotide sequence downstream from a promoter sequence, the vector preferably containing a marker (such as a resistance marker); Cellular organisms, or cell line, transformed with such a vector; A method of producing the product α-1,4-glucan lyase or any nucleotide sequence or part thereof coding for same, which comprises culturing such an organism (or cells from a cell line) transfected with such a vector and recovering the product.

Other modifications of the present invention will be apparent to those skilled in the art without departing from the scope of the invention.

We claim:

1. A method of preparing an a-1,4-glucan lyase having an amino acid sequence of SEQ ID NO:2, said method comprising the step of isolating a-1,4-glucan lyase from a fungally infected algae, said algae being *Gracilariopsis lemaneiformis* as identified by deposit CCAP 1373/1.

2. A method according to claim 1 wherein the α-1,4-glucan lyase is isolated and/or further purified using a gel that is not degraded by the α-1,4-glucan lyase.

3. A method according to claim 2, wherein the gel comprises dextrin or a cyclodextrin.

4. A α-1,4-glucan lyase enzyme prepared by the method of claim 1.

5. An isolated enzyme comprising an amino acid sequence of SEQ ID NO:2.

6. A method according to claim 3, wherein the gel comprises a cyclodextrin.

7. A method according to claim 6, wherein the gel comprises beta-cyclo-dextrin.

* * * * *

SEQUENCE LISTING (1) GENERAL INFORMATION:

(iii) NUMBER OF SEQUENCES: 25

(2) INFORMATION FOR SEQ ID NO:1:

```
    (i) SEQUENCE CHARACTERISTICS:
        (A) LENGTH: 1088 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Met Phe Ser Thr Leu Ala Phe Val Ala Pro Ser Ala Leu Gly Ala Ser
  1               5                  10                  15

Thr Phe Val Gly Ala Glu Val Arg Ser Asn Val Arg Ile His Ser Ala
                 20                  25                  30

Phe Pro Ala Val His Thr Ala Thr Arg Lys Thr Asn Arg Leu Asn Val
             35                  40                  45

Ser Met Thr Ala Leu Ser Asp Lys Gln Thr Thr Ala Gly Ser Thr
 50                  55                  60

Asp Asn Pro Asp Gly Ile Asp Tyr Lys Thr Tyr Asp Tyr Val Gly Val
 65                  70                  75                  80

Trp Gly Phe Ser Pro Leu Ser Asn Thr Asn Trp Phe Ala Ala Gly Ser
                 85                  90                  95

Ser Thr Pro Gly Gly Ile Thr Asp Trp Thr Ala Thr Met Asn Val Asn
                100                 105                 110

Phe Asp Arg Ile Asp Asn Pro Ser Ile Thr Val Gln His Pro Val Gln
            115                 120                 125

Val Gln Val Thr Ser Tyr Asn Asn Asn Ser Tyr Arg Val Arg Phe Asn
130                 135                 140

Pro Asp Gly Pro Ile Arg Asp Val Thr Arg Gly Pro Ile Leu Lys Gln
145                 150                 155                 160

Gln Leu Asp Trp Ile Arg Thr Gln Glu Leu Ser Glu Gly Cys Asp Pro
                165                 170                 175

Gly Met Thr Phe Thr Ser Glu Gly Phe Leu Thr Phe Glu Thr Lys Asp
                180                 185                 190

Leu Ser Val Ile Ile Tyr Gly Asn Phe Lys Thr Arg Val Thr Arg Lys
                195                 200                 205

Ser Asp Gly Lys Val Ile Met Glu Asn Asp Glu Val Gly Thr Ala Ser
210                 215                 220

Ser Gly Asn Lys Cys Arg Gly Leu Met Phe Val Asp Arg Leu Tyr Gly
225                 230                 235                 240

Asn Ala Ile Ala Ser Val Asn Lys Asn Phe Arg Asn Asp Ala Val Lys
                245                 250                 255

Gln Glu Gly Phe Tyr Gly Ala Gly Glu Val Asn Cys Lys Tyr Gln Asp
                260                 265                 270

Thr Tyr Ile Leu Glu Arg Thr Gly Ile Ala Met Thr Asn Tyr Asn Tyr
                275                 280                 285

Asp Asn Leu Asn Tyr Asn Gln Trp Asp Leu Arg Pro Pro His His Asp
                290                 295                 300

Gly Ala Leu Asn Pro Asp Tyr Tyr Ile Pro Met Tyr Ala Ala Pro
305                 310                 315                 320

Trp Leu Ile Val Asn Gly Cys Ala Gly Thr Ser Glu Gln Tyr Ser Tyr
                325                 330                 335

Gly Trp Phe Met Asp Asn Val Ser Gln Ser Tyr Met Asn Thr Gly Asp
                340                 345                 350

Thr Thr Trp Asn Ser Gly Gln Glu Asp Leu Ala Tyr Met Gly Ala Gln
                355                 360                 365
```

```
Tyr Gly Pro Phe Asp Gln His Phe Val Tyr Gly Ala Gly Gly Met
    370                 375                 380
Glu Cys Val Val Thr Ala Phe Ser Leu Leu Gln Gly Lys Glu Phe Glu
385                 390                 395                 400
Asn Gln Val Leu Asn Lys Arg Ser Val Met Pro Pro Lys Tyr Val Phe
                405                 410                 415
Gly Phe Phe Gln Gly Val Phe Gly Thr Ser Ser Leu Leu Arg Ala His
            420                 425                 430
Met Pro Ala Gly Glu Asn Asn Ile Ser Val Glu Glu Ile Val Glu Gly
        435                 440                 445
Tyr Gln Asn Asn Asn Phe Pro Phe Glu Gly Leu Ala Val Asp Val Asp
    450                 455                 460
Met Gln Asp Asn Leu Arg Val Phe Thr Thr Lys Gly Glu Phe Trp Thr
465                 470                 475                 480
Ala Asn Arg Val Gly Thr Gly Gly Asp Pro Asn Asn Arg Ser Val Phe
                485                 490                 495
Glu Trp Ala His Asp Lys Gly Leu Val Cys Gln Thr Asn Ile Thr Cys
            500                 505                 510
Phe Leu Arg Asn Asp Asn Glu Gly Gln Asp Tyr Glu Val Asn Gln Thr
        515                 520                 525
Leu Arg Glu Arg Gln Leu Tyr Thr Lys Asn Asp Ser Leu Thr Gly Thr
    530                 535                 540
Asp Phe Gly Met Thr Asp Asp Gly Pro Ser Asp Ala Tyr Ile Gly His
545                 550                 555                 560
Leu Asp Tyr Gly Gly Val Glu Cys Asp Ala Leu Phe Pro Asp Trp
                565                 570                 575
Gly Arg Pro Asp Val Ala Glu Trp Trp Gly Asn Asn Tyr Lys Lys Leu
            580                 585                 590
Phe Ser Ile Gly Leu Asp Phe Val Trp Gln Asp Met Thr Val Pro Ala
        595                 600                 605
Met Met Pro His Lys Ile Gly Asp Asp Ile Asn Val Lys Pro Asp Gly
    610                 615                 620
Asn Trp Pro Asn Ala Asp Asp Pro Ser Asn Gly Gln Tyr Asn Trp Lys
625                 630                 635                 640
Thr Tyr His Pro Gln Val Leu Val Thr Asp Met Arg Tyr Glu Asn His
                645                 650                 655
Gly Arg Glu Pro Met Val Thr Gln Arg Asn Ile His Ala Tyr Thr Leu
            660                 665                 670
Cys Glu Ser Thr Arg Lys Glu Gly Ile Val Glu Asn Ala Asp Thr Leu
        675                 680                 685
Thr Lys Phe Arg Arg Ser Tyr Ile Ile Ser Arg Gly Tyr Ile Gly
    690                 695                 700
Asn Gln His Phe Gly Gly Met Trp Val Gly Asp Asn Ser Thr Thr Ser
705                 710                 715                 720
Asn Tyr Ile Gly Met Met Ile Ala Asn Asn Ile Asn Met Asn Met Ser
                725                 730                 735
Cys Leu Pro Leu Val Gly Ser Asp Ile Gly Phe Thr Ser Tyr Asp
            740                 745                 750
Asn Glu Asn Gln Arg Thr Pro Cys Thr Gly Asp Leu Met Val Arg Tyr
        755                 760                 765
Val Gln Ala Gly Cys Leu Leu Pro Trp Phe Arg Asn His Tyr Asp Arg
    770                 775                 780
Trp Ile Glu Ser Lys Asp His Gly Lys Asp Tyr Gln Glu Leu Tyr Met
785                 790                 795                 800
```

```
Tyr Pro Asn Glu Met Asp Thr Leu Arg Lys Phe Val Glu Phe Arg Tyr
                805                 810                 815
Arg Trp Gly Glu Val Leu Tyr Thr Ala Met Tyr Gln Asn Ala Ala Phe
                820                 825                 830
Gly Lys Pro Ile Ile Lys Ala Ala Ser Met Tyr Asn Asn Asp Ser Asn
                835                 840                 845
Val Arg Arg Ala Gln Asn Asp His Phe Leu Leu Gly Gly His Asp Gly
    850                 855                 860
Tyr Arg Ile Leu Cys Ala Pro Val Val Trp Glu Asn Ser Thr Glu Arg
865                 870                 875                 880
Glu Leu Tyr Leu Pro Val Leu Thr Gln Trp Tyr Lys Phe Gly Pro Asp
                885                 890                 895
Phe Asp Thr Lys Pro Leu Glu Gly Ala Met Asn Gly Gly Asp Arg Ile
                900                 905                 910
Tyr Asn Tyr Pro Val Pro Gln Ser Glu Ser Pro Ile Phe Val Arg Glu
                915                 920                 925
Gly Ala Ile Leu Pro Thr Arg Tyr Thr Leu Asn Gly Glu Asn Lys Ser
                930                 935                 940
Leu Asn Thr Tyr Thr Asp Glu Asp Pro Leu Val Phe Glu Val Phe Pro
945                 950                 955                 960
Leu Gly Asn Asn Arg Ala Asp Gly Met Cys Tyr Leu Asp Asp Gly Gly
                965                 970                 975
Val Thr Thr Asn Ala Glu Asp Asn Gly Lys Phe Ser Val Val Lys Val
                980                 985                 990
Ala Ala Glu Gln Asp Gly Gly Thr Glu Thr Ile Thr Phe Thr Asn Asp
                995                1000                1005
Cys Tyr Glu Tyr Val Phe Gly Gly Pro Phe Tyr Val Arg Val Arg Gly
    1010                1015                1020
Ala Gln Ser Pro Ser Asn Ile His Val Ser Ser Gly Ala Gly Ser Gln
025                 1030                1035                1040
Asp Met Lys Val Ser Ser Ala Thr Ser Arg Ala Ala Leu Phe Asn Asp
                1045                1050                1055
Gly Glu Asn Gly Asp Phe Trp Val Asp Gln Glu Thr Asp Ser Leu Trp
                1060                1065                1070
Leu Lys Leu Pro Asn Val Val Leu Pro Asp Ala Val Ile Thr Ile Thr
                1075                1080                1085

(2) INFORMATION FOR SEQ ID NO:2:

(i) SEQUENCE CHARACTERISTICS:
        (A) LENGTH: 1091 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Tyr Pro Thr Leu Thr Phe Val Ala Pro Ser Ala Leu Gly Ala Arg
  1               5                  10                  15
Thr Phe Thr Cys Val Gly Ile Phe Arg Ser His Ile Leu Ile His Ser
                 20                  25                  30
Val Val Pro Ala Val Arg Leu Ala Val Arg Lys Ser Asn Arg Leu Asn
             35                  40                  45
Val Ser Met Ser Ala Leu Phe Asp Lys Pro Thr Ala Val Thr Gly Gly
         50                  55                  60
```

```
Lys Asp Asn Pro Asp Asn Ile Asn Tyr Thr Thr Tyr Asp Tyr Val Pro
 65                  70                  75                  80

Val Trp Arg Phe Asp Pro Leu Ser Asn Thr Asn Trp Phe Ala Ala Gly
                 85                  90                  95

Ser Ser Thr Pro Gly Asp Ile Asp Trp Thr Ala Thr Met Asn Val
            100                 105                 110

Asn Phe Asp Arg Ile Asp Asn Pro Ser Phe Thr Leu Glu Leu Pro Val
            115                 120                 125

Gln Val Gln Val Thr Ser Tyr Lys Asn Asn Cys Phe Arg Val Arg Phe
        130                 135                 140

Asn Pro Asp Gly Pro Ile Arg Asp Val Asp Arg Gly Pro Ile Leu Gln
145                 150                 155                 160

Gln Gln Leu Asn Trp Ile Arg Lys Gln Glu Gln Ser Lys Gly Phe Asp
                165                 170                 175

Pro Lys Met Gly Phe Thr Lys Glu Gly Phe Leu Lys Phe Glu Thr Lys
            180                 185                 190

Asp Leu Asn Val Ile Ile Tyr Gly Asn Phe Lys Thr Arg Val Thr Arg
            195                 200                 205

Lys Arg Asp Gly Lys Gly Ile Met Glu Asn Asn Glu Val Pro Ala Gly
        210                 215                 220

Ser Leu Gly Asn Lys Cys Arg Gly Leu Met Phe Val Asp Arg Leu Tyr
225                 230                 235                 240

Gly Thr Ala Ile Ala Ser Val Asn Glu Asn Tyr Arg Asn Asp Pro Asp
                245                 250                 255

Arg Lys Glu Gly Phe Tyr Gly Ala Gly Glu Val Asn Cys Glu Phe Trp
            260                 265                 270

Asp Ser Glu Gln Asn Arg Asn Lys Tyr Ile Leu Glu Arg Thr Gly Ile
        275                 280                 285

Ala Met Thr Asn Tyr Asn Tyr Asp Asn Tyr Asn Gln Ser Asp
290                 295                 300

Leu Ile Ala Pro Gly Tyr Pro Ser Asp Pro Asn Phe Tyr Ile Pro Met
305                 310                 315                 320

Tyr Phe Ala Ala Pro Trp Val Val Lys Gly Cys Ser Gly Asn Ser
                325                 330                 335

Asp Glu Gln Tyr Ser Tyr Gly Trp Phe Met Asp Asn Val Ser Gln Thr
            340                 345                 350

Tyr Met Asn Thr Gly Gly Thr Ser Trp Asn Cys Gly Glu Glu Asn Leu
            355                 360                 365

Ala Tyr Met Gly Ala Gln Cys Gly Pro Phe Asp Gln His Phe Val Tyr
        370                 375                 380

Gly Asp Gly Asp Gly Leu Glu Asp Val Val Gln Ala Phe Ser Leu Leu
385                 390                 395                 400

Gln Gly Lys Glu Phe Glu Asn Gln Val Leu Asn Lys Arg Ala Val Met
                405                 410                 415

Pro Pro Lys Tyr Val Phe Gly Tyr Phe Gln Gly Val Phe Gly Ile Ala
            420                 425                 430

Ser Leu Leu Arg Glu Gln Arg Pro Glu Gly Gly Asn Asn Ile Ser Val
        435                 440                 445

Gln Glu Ile Val Glu Gly Tyr Gly Ser Asn Asn Phe Pro Leu Glu Gly
        450                 455                 460

Leu Ala Val Asp Val Asp Met Gln Gln Asp Leu Arg Val Phe Thr Thr
465                 470                 475                 480

Lys Ile Glu Phe Trp Thr Ala Asn Lys Val Gly Thr Gly Asp Ser
                485                 490                 495
```

```
Asn Asn Lys Ser Val Phe Glu Trp Ala His Asp Lys Gly Leu Val Cys
        500                 505                 510

Gln Thr Asn Val Thr Cys Phe Leu Arg Asn Asp Asn Gly Gly Ala Asp
        515                 520                 525

Tyr Glu Val Asn Gln Thr Leu Arg Glu Lys Gly Leu Tyr Thr Lys Asn
        530                 535                 540

Asp Ser Leu Thr Asn Thr Asn Phe Gly Thr Thr Asn Asp Gly Pro Ser
545                 550                 555                 560

Asp Ala Tyr Ile Gly His Leu Asp Tyr Gly Gly Gly Asn Cys Asp
                565                 570                 575

Ala Leu Phe Pro Asp Trp Gly Arg Pro Gly Val Ala Glu Trp Trp Gly
        580                 585                 590

Asp Asn Tyr Ser Lys Leu Phe Lys Ile Gly Leu Asp Phe Val Trp Gln
        595                 600                 605

Asp Met Thr Val Pro Ala Met Met Pro His Lys Val Gly Asp Ala Val
        610                 615                 620

Asp Thr Arg Ser Pro Tyr Gly Trp Pro Asn Glu Asn Asp Pro Ser Asn
625                 630                 635                 640

Gly Arg Tyr Asn Trp Lys Ser Tyr His Pro Gln Val Leu Val Thr Asp
                645                 650                 655

Met Arg Tyr Glu Asn His Gly Arg Glu Pro Met Phe Thr Gln Arg Asn
        660                 665                 670

Met His Ala Tyr Thr Leu Cys Glu Ser Thr Arg Lys Glu Gly Ile Val
        675                 680                 685

Ala Asn Ala Asp Thr Leu Thr Lys Phe Arg Arg Ser Tyr Ile Ile Ser
        690                 695                 700

Arg Gly Gly Tyr Ile Gly Asn Gln His Phe Gly Gly Met Trp Val Gly
705                 710                 715                 720

Asp Asn Ser Ser Ser Gln Arg Tyr Leu Gln Met Met Ile Ala Asn Ile
                725                 730                 735

Val Asn Met Asn Met Ser Cys Leu Pro Leu Val Gly Ser Asp Ile Gly
        740                 745                 750

Gly Phe Thr Ser Tyr Asp Gly Arg Asn Val Cys Pro Gly Asp Leu Met
        755                 760                 765

Val Arg Phe Val Gln Ala Gly Cys Leu Leu Pro Trp Phe Arg Asn His
        770                 775                 780

Tyr Gly Arg Leu Val Glu Gly Lys Gln Glu Gly Lys Tyr Tyr Gln Glu
785                 790                 795                 800

Leu Tyr Met Tyr Lys Asp Glu Met Ala Thr Leu Arg Lys Phe Ile Glu
                805                 810                 815

Phe Arg Tyr Arg Trp Gln Glu Val Leu Tyr Thr Ala Met Tyr Gln Asn
        820                 825                 830

Ala Ala Phe Gly Lys Pro Ile Ile Lys Ala Ala Ser Met Tyr Asp Asn
        835                 840                 845

Asp Arg Asn Val Arg Gly Ala Gln Asp Asp His Phe Leu Leu Gly Gly
        850                 855                 860

His Asp Gly Tyr Arg Ile Leu Cys Ala Pro Val Val Trp Glu Asn Thr
865                 870                 875                 880

Thr Ser Arg Asp Leu Tyr Leu Pro Val Leu Thr Lys Trp Tyr Lys Phe
                885                 890                 895

Gly Pro Asp Tyr Asp Thr Lys Arg Leu Asp Ser Ala Leu Asp Gly Gly
        900                 905                 910
```

```
Gln Met Ile Lys Asn Tyr Ser Val Pro Gln Ser Asp Ser Pro Ile Phe
        915                 920                 925

Val Arg Glu Gly Ala Ile Leu Pro Thr Arg Tyr Thr Leu Asp Gly Ser
        930                 935                 940

Asn Lys Ser Met Asn Thr Tyr Thr Asp Lys Asp Pro Leu Val Phe Glu
945                 950                 955                 960

Val Phe Pro Leu Gly Asn Asn Arg Ala Asp Gly Met Cys Tyr Leu Asp
                965                 970                 975

Asp Gly Gly Ile Thr Thr Asp Ala Glu Asp His Gly Lys Phe Ser Val
            980                 985                 990

Ile Asn Val Glu Ala Leu Arg Lys Gly Val Thr Thr Thr Ile Lys Phe
        995                 1000                1005

Ala Tyr Asp Thr Tyr Gln Tyr Val Phe Asp Gly Pro Phe Tyr Val Arg
    1010                1015                1020

Ile Arg Asn Leu Thr Thr Ala Ser Lys Ile Asn Val Ser Ser Gly Ala
025                 1030                1035                1040

Gly Glu Glu Asp Met Thr Pro Thr Ser Ala Asn Ser Arg Ala Ala Leu
                1045                1050                1055

Phe Ser Asp Gly Gly Val Gly Glu Tyr Trp Ala Asp Asn Asp Thr Ser
            1060                1065                1070

Ser Leu Trp Met Lys Leu Pro Asn Leu Val Leu Gln Asp Ala Val Ile
    1075                1080                1085

Thr Ile Thr
    1090

(2) INFORMATION FOR SEQ ID NO:3:

(i) SEQUENCE CHARACTERISTICS:
        (A) LENGTH: 3267 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:3:

ATGTTTTCAA CCCTTGCGTT TGTCGCACCT AGTGCGCTGG GAGCCAGTAC CTTCGTAGGG    60

GCGGAGGTCA GGTCAAATGT TCGTATCCAT TCCGCTTTTC CAGCTGTGCA CACAGCTACT   120

CGCAAAACCA ATCGCCTCAA TGTATCCATG ACCGCATTGT CCGACAAACA AACGGCTACT   180

GCGGGTAGTA CAGACAATCC GGACGGTATC GACTACAAGA CCTACGATTA CGTCGGAGTA   240

TGGGGTTTCA GCCCCCTCTC CAACACGAAC TGGTTTGCTG CCGGCTCTTC TACCCCGGGT   300

GGCATCACTG ATTGGACGGC TACAATGAAT GTCAACTTCG ACCGTATCGA CAATCCGTCC   360

ATCACTGTCC AGCATCCCGT TCAGGTTCAG GTCACGTCAT ACAACAACAA CAGCTACAGG   420

GTTCGCTTCA ACCCTGATGG CCCTATTCGT GATGTGACTC GTGGGCCTAT CCTCAAGCAG   480

CAACTAGATT GGATTCGAAC GCAGGAGCTG TCAGAGGGAT GTGATCCCGG AATGACTTTC   540

ACATCAGAAG GTTTCTTGAC TTTTGAGACC AAGGATCTAA GCGTCATCAT CTACGGAAAT   600

TTCAAGACCA GAGTTACGAG AAAGTCTGAC GGCAAGGTCA TCATGGAAAA TGATGAAGTT   660

GGAACTGCAT CGTCCGGGAA CAAGTGCCGG GGATTGATGT TCGTTGATAG ATTATACGGT   720

AACGCTATCG CTTCCGTCAA CAAGAACTTC CGCAACGACG CGGTCAAGCA GGAGGGATTC   780

TATGGTGCAG GTGAAGTCAA CTGTAAGTAC CAGGACACCT ACATCTTAGA ACGCACTGGA   840

ATCGCCATGA CAAATTACAA CTACGATAAC TTGAACTATA ACCAGTGGGA CCTTAGACCT   900

CCGCATCATG ATGGTGCCCT CAACCCAGAC TATTATATTC CAATGTACTA CGCAGCACCT   960
```

```
TGGTTGATCG TTAATGGATG CGCCGGTACT TCGGAGCAGT ACTCGTATGG ATGGTTCATG    1020

GACAATGTCT CTCAATCTTA CATGAATACT GGAGATACTA CCTGGAATTC TGGACAAGAG    1080

GACCTGGCAT ACATGGGCGC GCAGTATGGA CCATTTGACC AACATTTTGT TTACGGTGCT    1140

GGGGGTGGGA TGGAATGTGT GGTCACAGCG TTCTCTCTTC TACAAGGCAA GGAGTTCGAG    1200

AACCAAGTTC TCAACAAACG TTCAGTAATG CCTCCGAAAT ACGTCTTTGG TTTCTTCCAG    1260

GGTGTTTTCG GGACTTCTTC CTTGTTGAGA GCGCATATGC CAGCAGGTGA GAACAACATC    1320

TCAGTCGAAG AAATTGTAGA AGGTTATCAA ACAACAATT TCCCTTTCGA GGGGCTCGCT    1380

GTGGACGTGG ATATGCAAGA CAACTTGCGG GTGTTCACCA CGAAGGGCGA ATTTTGGACC    1440

GCAAACAGGG TGGGTACTGG CGGGGATCCA ACAACCGAT CGGTTTTTGA ATGGGCACAT    1500

GACAAAGGCC TTGTTTGTCA GACAAATATA ACTTGCTTCC TGAGGAATGA TAACGAGGGG    1560

CAAGACTACG AGGTCAATCA GACGTTAAGG GAGAGGCAGT TGTACACGAA GAACGACTCC    1620

CTGACGGGTA CGGATTTTGG AATGACCGAC GACGGCCCCA GCGATGCGTA CATCGGTCAT    1680

CTGGACTATG GGGGTGGAGT AGAATGTGAT GCACTTTTCC CAGACTGGGG ACGGCCTGAC    1740

GTGGCCGAAT GGTGGGAAA TAACTATAAG AAACTGTTCA GCATTGGTCT CGACTTCGTC    1800

TGGCAAGACA TGACTGTTCC AGCAATGATG CCGCACAAAA TTGGCGATGA CATCAATGTG    1860

AAACCGGATG GGAATTGGCC GAATGCGGAC GATCCGTCCA ATGGACAATA CAACTGGAAG    1920

ACGTACCATC CCCAAGTGCT TGTAACTGAT ATGCGTTATG AGAATCATGG TCGGGAACCG    1980

ATGGTCACTC AACGCAACAT TCATGCGTAT ACACTGTGCG AGTCTACTAG GAAGGAAGGG    2040

ATCGTGGAAA ACGCAGACAC TCTAACGAAG TTCCGCCGTA GCTACATTAT CAGTCGTGGT    2100

GGTTACATTG GTAACCAGCA TTTCGGGGGT ATGTGGGTGG GAGACAACTC TACTACATCA    2160

AACTACATCC AAATGATGAT TGCCAACAAT ATTAACATGA ATATGTCTTG CTTGCCTCTC    2220

GTCGGCTCCG ACATTGGAGG ATTCACCTCA TACGACAATG AGAATCAGCG AACGCCGTGT    2280

ACCGGGGACT TGATGGTGAG GTATGTGCAG GCGGGCTGCC TGTTGCCGTG GTTCAGGAAC    2340

CACTATGATA GGTGGATCGA GTCCAAGGAC CACGGAAAGG ACTACCAGGA GCTGTACATG    2400

TATCCGAATG AAATGGATAC GTTGAGGAAG TTCGTTGAAT TCCGTTATCG CTGGCAGGAA    2460

GTGTTGTACA CGGCCATGTA CCAGAATGCG GCTTTCGGAA AGCCGATTAT CAAGGCTGCT    2520

TCGATGTACA ATAACGACTC AAACGTTCGC AGGGCGCAGA ACGATCATTT CCTTCTTGGT    2580

GGACATGATG GATATCGCAT TCTGTGCGCG CCTGTTGTGT GGGAGAATTC GACCGAACGC    2640

GAATTGTACT TGCCCGTGCT GACCCAATGG TACAAATTCG GTCCCGACTT TGACACCAAG    2700

CCTCTGGAAG GAGCGATGAA CGGAGGGGAC CGAATTTACA ACTACCCTGT ACCGCAAAGT    2760

GAATCACCAA TCTTCGTGAG AGAAGGTGCG ATTCTCCCTA CCCGCTACAC GTTGAACGGT    2820

GAAAACAAAT CATTGAACAC GTACACGGAC GAAGATCCGT TGGTGTTTGA AGTATTCCCC    2880

CTCGGAAACA ACCGTGCCGA CGGTATGTGT TATCTTGATG ATGGCGGTGT GACCACCAAT    2940

GCTGAAGACA ATGGCAAGTT CTCTGTCGTC AAGGTGGCAG CGGAGCAGGA TGGTGGTACG    3000

GAGACGATAA CGTTTACGAA TGATTGCTAT GAGTACGTTT TCGGTGGACC GTTCTACGTT    3060

CGAGTGCGCG GCGCTCAGTC GCCGTCGAAC ATCCACGTGT CTTCTGGAGC GGGTTCTCAG    3120

GACATGAAGG TGAGCTCTGC CACTTCCAGG GCTGCGCTGT TCAATGACGG GGAGAACGGT    3180

GATTTCTGGG TTGACCAGGA GACAGATTCT CTGTGGCTGA AGTTGCCCAA CGTTGTTCTC    3240

CCGGACGCTG TGATCACAAT TACCTAA                                        3267
```

(2) INFORMATION FOR SEQ ID NO:4:

(i) SEQUENCE CHARACTERISTICS:
        (A) LENGTH: 3276 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:4:

```
ATGTATCCAA CCCTCACCTT CGTGGCGCCT AGTGCGCTAG GGGCCAGAAC TTTCACGTGT    60
GTGGGCATTT TTAGGTCACA CATTCTTATT CATTCGGTTG TTCCAGCGGT GCGTCTAGCT   120
GTGCGCAAAA GCAACCGCCT CAATGTATCC ATGTCCGCTT TGTTCGACAA ACCGACTGCT   180
GTTACTGGAG GGAAGGACAA CCCGGACAAT ATCAATTACA CCACTTATGA CTACGTCCCT   240
GTGTGGCGCT TCGACCCCCT CAGCAATACG AACTGGTTTG CTGCCGGATC TTCCACTCCC   300
GGCGATATTG ACGACTGGAC GGCGACAATG AATGTGAACT TCGACCGTAT CGACAATCCA   360
TCCTTCACTC TCGAGAAACC GGTTCAGGTT CAGGTCACGT CATACAAGAA CAATTGTTTC   420
AGGGTTCGCT TCAACCCTGA TGGTCCTATT CGCGATGTGG ATCGTGGGCC TATCCTCCAG   480
CAGCAACTAA ATTGGATCCG GAAGCAGGAG CAGTCGAAGG GGTTTGATCC TAAGATGGGC   540
TTCACAAAAG AAGGTTTCTT GAAATTTGAG ACCAAGGATC TGAACGTTAT CATATATGGC   600
AATTTTAAGA CTAGAGTTAC GAGGAAGAGG GATGGAAAAG GGATCATGGA GAATAATGAA   660
GTGCCGGCAG GATCGTTAGG GAACAAGTGC CGGGGATTGA TGTTTGTCGA CAGGTTGTAC   720
GGCACTGCCA TCGCTTCCGT TAATGAAAAT TACCGCAACG ATCCCGACAG GAAAGAGGGG   780
TTCTATGGTG CAGGAGAAGT AAACTGCGAG TTTTGGGACT CCGAACAAAA CAGGAACAAG   840
TACATCTTAG AACGAACTGG AATCGCCATG ACAAATTACA ATTATGACAA CTATAACTAC   900
AACCAGTCAG ATCTTATTGC TCCAGGATAT CCTTCCGACC CGAACTTCTA CATTCCCATG   960
TATTTTGCAG CACCTTGGGT AGTTGTTAAG GGATGCAGTG GCAACAGCGA TGAACAGTAC  1020
TCGTACGGAT GGTTTATGGA TAATGTCTCC CAAACTTACA TGAATACTGG TGGTACTTCC  1080
TGGAACTGTG GAGAGGAGAA CTTGGCATAC ATGGGAGCAC AGTGCGGTCC ATTTGACCAA  1140
CATTTTGTGT ATGGTGATGG AGATGGTCTT GAGGATGTTG TCCAAGCGTT CTCTCTTCTG  1200
CAAGGCAAAG AGTTTGAGAA CCAAGTTCTG AACAAACGTG CCGTAATGCC TCCGAAATAT  1260
GTGTTTGGTT ACTTTCAGGG AGTCTTTGGG ATTGCTTCCT TGTTGAGAGA GCAAAGACCA  1320
GAGGGTGGTA ATAACATCTC TGTTCAAGAG ATTGTCGAAG GTTACCAAAG CAATAACTTC  1380
CCTTTAGAGG GGTTAGCCGT AGATGTGGAT ATGCAACAAG ATTTGCGCGT GTTCACCACG  1440
AAGATTGAAT TTTGGACGGC AAATAAGGTA GGCACCGGGG GAGACTCGAA TAACAAGTCG  1500
GTGTTTGAAT GGGCACATGA CAAAGGCCTT GTATGTCAGA CGAATGTTAC TTGCTTCTTG  1560
AGAAACGACA ACGGCGGGGC AGATTACGAA GTCAATCAGA CATTGAGGGA GAAGGGTTTG  1620
TACACGAAGA ATGACTCACT GACGAACACT AACTTCGGAA CTACCAACGA CGGGCCGAGC  1680
GATGCGTACA TTGGACATCT GGACTATGGT GGCGGAGGGA ATTGTGATGC ACTTTTCCCA  1740
GACTGGGGTC GACCGGGTGT GGCTGAATGG TGGGGTGATA ACTACAGCAA GCTCTTCAAA  1800
ATTGGTCTGG ATTTCGTCTG GCAAGACATG ACAGTTCCAG CTATGATGCC ACACAAAGTT  1860
GGCGACGCAG TCGATACGAG ATCACCTTAC GGCTGGCCGA ATGAGAATGA TCCTTCGAAC  1920
GGACGATACA ATTGGAAATC TTACCATCCA CAAGTTCTCG TAACTGATAT GCGATATGAG  1980
AATCATGGAA GGGAACCGAT GTTCACTCAA CGCAATATGC ATGCGTACAC ACTCTGTGAA  2040
```

```
TCTACGAGGA AGGAAGGGAT GTTGCAAAT GCAGACACTC TAACGAAGTT CCGCCGCAGT      2100

TATATTATCA GTCGTGGAGG TTACATTGGC AACCAGCATT TTGGAGGAAT GTGGGTTGGA      2160

GACAACTCTT CCTCCCAAAG ATACCTCCAA ATGATGATCG CGAACATCGT CAACATGAAC      2220

ATGTCTTGCC TTCCACTAGT TGGGTCCGAC ATTGGAGGTT TTACTTCGTA TGATGGACGA      2280

AACGTGTGTC CCGGGGATCT AATGGTAAGA TTCGTGCAGG CGGGTTGCTT ACTACCGTGG      2340

TTCAGAAACC ACTATGGTAG GTTGGTCGAG GGCAAGCAAG AGGGAAAATA CTATCAAGAA      2400

CTGTACATGT ACAAGGACGA GATGGCTACA TTGAGAAAAT TCATTGAATT CCGTTACCGC      2460

TGGCAGGAGG TGTTGTACAC TGCTATGTAC CAGAATGCGG CTTTCGGGAA ACCGATTATC      2520

AAGGCAGCTT CCATGTACGA CAACGACAGA AACGTTCGCG GCGCACAGGA TGACCACTTC      2580

CTTCTCGGCG GACACGATGG ATATCGTATT TTGTGTGCAC CTGTTGTGTG GGAGAATACA      2640

ACCAGTCGCG ATCTGTACTT GCCTGTGCTG ACCAAATGGT ACAAATTCGG CCCTGACTAT      2700

GACACCAAGC GCCTGGATTC TGCGTTGGAT GGAGGGCAGA TGATTAAGAA CTATTCTGTG      2760

CCACAAAGCG ACTCTCCGAT ATTTGTGAGG GAAGGAGCTA TTCTCCCTAC CCGCTACACG      2820

TTGGACGGTT CGAACAAGTC AATGAACACG TACACAGACA AGACCCGTT GGTGTTTGAG       2880

GTATTCCCTC TTGGAAACAA CCGTGCCGAC GGTATGTGTT ATCTTGATGA TGGCGGTATT      2940

ACTACAGATG CTGAGGACCA TGGCAAATTC TCTGTTATCA ATGTCGAAGC CTTACGGAAA      3000

GGTGTTACGA CGACGATCAA GTTTGCGTAT GACACTTATC AATACGTATT TGATGGTCCA      3060

TTCTACGTTC GAATCCGTAA TCTTACGACT GCATCAAAAA TTAACGTGTC TTCTGGAGCG      3120

GGTGAAGAGG ACATGACACC GACCTCTGCG AACTCGAGGG CAGCTTTGTT CAGTGATGGA      3180

GGTGTTGGAG AATACTGGGC TGACAATGAT ACGTCTTCTC TGTGGATGAA GTTGCCAAAC      3240

CTGGTTCTGC AAGACGCTGT GATTACCATT ACGTAG                                3276

(2) INFORMATION FOR SEQ ID NO:5:

(i) SEQUENCE CHARACTERISTICS:
        (A) LENGTH: 90 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Tyr Arg Trp Gln Glu Val Leu Tyr Thr Ala Met Tyr Gln Asn Ala Ala
 1               5                  10                  15

Phe Gly Lys Pro Ile Ile Lys Ala Ala Ser Met Tyr Asn Asn Asp Ser
            20                  25                  30

Asn Val Arg Arg Ala Gln Asn Asp His Phe Leu Leu Gly Gly His Asp
        35                  40                  45

Gly Tyr Arg Ile Leu Cys Ala Pro Val Val Trp Glu Asn Ser Thr Glu
    50                  55                  60

Arg Glu Leu Tyr Leu Pro Val Leu Thr Gln Trp Tyr Lys Phe Gly Pro
65                  70                  75                  80

Asp Phe Asp Thr Lys Pro Leu Glu Gly Ala
            85                  90

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
```

```
            (D) TOPOLOGY: linear (ii) MOLECULE TYPE: Genomic DNA (ix) FEATURE:
            (A) NAME/KEY: Other
            (B) LOCATION: 18...18
            (D) OTHER INFORMATION: N is G or A or T or C (xi) SEQUENCE DESCRIPTION: SEQ ID NO:6:

ATGTAYAAYA AYGAYTCNAA YGT                                              23

(2) INFORMATION FOR SEQ ID NO:7:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: Genomic DNA (ix) FEATURE:

(xi) SEQUENCE DESCRIPTION: SEQ ID NO:7:

ATGTAYAAYA AYGAYAGYAA YGT                                              23

(2) INFORMATION FOR SEQ ID NO:8:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Genomic DNA (ix) FEATURE:
            (A) NAME/KEY: Other
            (B) LOCATION: 3...3
            (D) OTHER INFORMATION: N is G or A or T or C
            (A) NAME/KEY: Other
            (B) LOCATION: 12...12
            (D) OTHER INFORMATION: N is G or A or T or C
            (A) NAME/KEY: Other
            (B) LOCATION: 15...15
            (D) OTHER INFORMATION: N is G or A or T or C (xi) SEQUENCE DESCRIPTION: SEQ ID NO:8:

TANCCRTCRT GNCCNCC                                                     17

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Genomic DNA (ix) FEATURE:
            (A) NAME/KEY: Other
            (B) LOCATION: 3...3
            (D) OTHER INFORMATION: N is G or A or T or C (xi) SEQUENCE DESCRIPTION: SEQ ID NO:9:

GGNCCRAAYT TRTACCAYTG                                                  20

(2) INFORMATION FOR SEQ ID NO:10:

(i) SEQUENCE CHARACTERISTICS:
```

```
        (A) LENGTH: 17 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Other
        (B) LOCATION: 6...6
        (D) OTHER INFORMATION: N is G or A or T or C (xi) SEQUENCE DESCRIPTION: SEQ ID NO:10:

TAYCGNTGGC ARGARGT                                                  17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Genomic DNA (ix) FEATURE:

(xi) SEQUENCE DESCRIPTION: SEQ ID NO:11:

TAYAGRTGGC ARGARGT                                                  17

(2) INFORMATION FOR SEQ ID NO:12:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:12:

ATGTACAACA ACGACTCGAA CGTTCGCAGG GCGCAGAACG ATCATTTCCT TCTTGGCGGC    60

CACGACGGTT A                                                        71

(2) INFORMATION FOR SEQ ID NO:13:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Met Tyr Asn Asn Asp Ser Asn Val Arg Arg Ala Gln Asn Asp His Phe
1               5                   10                  15

Leu Leu Gly Gly His Asp Gly
            20

(2) INFORMATION FOR SEQ ID NO:14:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: Genomic DNA
```

(xi) SEQUENCE DESCRIPTION: SEQ ID NO:14:

ATGTACAACA ACGACTCGAA CGTTCGCAGG GCGCAGAACG ATCATTTCCT TCTTGGTGGA    60

CATGATGGAT ATCGCATTCT GTGCGCGCCT GTTGTGTGGG AGAATTCGAC CGAACGGAAT    120

TGTACTTGCC CGTGCTGACC CAATGGTACA AATTCGGCCC                           160

(2) INFORMATION FOR SEQ ID NO:15:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Met Tyr Asn Asn Asp Ser Asn Val Arg Arg Ala Gln Asn Asp His Phe
 1               5                  10                  15

Leu Leu Gly Gly His Asp Gly Tyr Arg Ile Leu Cys Ala Pro Val Val
            20                  25                  30

Trp Glu Asn Ser Thr Glu Arg Glu Leu Tyr Leu Pro Val Leu Thr Gln
        35                  40                  45

Trp Tyr Lys Phe Gly Pro
        50
```

(2) INFORMATION FOR SEQ ID NO:16:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:16:

TACAGGTGGC AGGAGGTGTT GTACACTGCT ATGTACCAGA ATGCGGCTTT CGGGAAACCG    60

ATTATCAAGG CAGCTTCCAT GTACGACAAC GACAGAAACG TTCGCGGCGC ACAGGATGAC    120

CACTTCCTTC TCGGCGGACA CGATGGATAT CGTATTTTGT GTGCACCTGT TGTGTGGAG    180

AATACAACCA GTCGCGATCT GTACTTGCCT GTGCTGACCA GTGGTACAAA TTCGGCCC    238

(2) INFORMATION FOR SEQ ID NO:17:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Tyr Arg Trp Gln Glu Val Leu Tyr Thr Ala Met Tyr Gln Asn Ala Ala
 1               5                  10                  15

Phe Gly Lys Pro Ile Ile Lys Ala Ala Ser Met Tyr Asp Asn Asp Arg
            20                  25                  30

Asn Val Arg Gly Ala Gln Asp Asp His Phe Leu Leu Gly Gly His Asp
        35                  40                  45

Gly Tyr Arg Ile Leu Cys Ala Pro Val Val Trp Glu Asn Thr Thr Ser
    50                  55                  60
```

Arg Asp Leu Tyr Leu Pro Val Leu Thr Lys Trp Tyr Lys Phe Gly
65              70              75

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:18:

GCTCTAGAGC ATGTTTTCAA CCCTTGCG                              28

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:19:

AGCTTGTTAA CATGTATCCA ACCCTCACCT TCGTGG                     36

(2) INFORMATION FOR SEQ ID NO:20:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:20:

ACAATTGTAC ATAGGTTGGG AGTGGAAGCA CCGC                       34

(2) INFORMATION FOR SEQ ID NO:21:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Met Tyr Asn Asn Asp Ser Asn Val
1               5

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Gly Gly His Asp Gly Tyr
1               5

```
(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Gln Trp Tyr Lys Phe Gly
 1               5

(2) INFORMATION FOR SEQ ID NO:24:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Tyr Arg Trp Gln Glu Val
 1               5

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Thr Ala Leu Ser Asp Lys Gln Thr Ala
 1               5
```